US008513430B2

(12) United States Patent
Polisetti et al.

(10) Patent No.: US 8,513,430 B2
(45) Date of Patent: Aug. 20, 2013

(54) SUBSTITUTED THIAZOL-2-YLAMINE DERIVATIVES, PHARMACEUTICAL COMPOSITIONS, AND METHODS OF USE AS 11-BETA HSD1 MODULATORS

(75) Inventors: Dharma Rao Polisetti, High Point, NC (US); Suparna Gupta, Greensboro, NC (US)

(73) Assignee: High Point Pharmaceuticals, LLC, High Point, NC (US)

( * ) Notice: Subject to any disclaimer, the term of this patent is extended or adjusted under 35 U.S.C. 154(b) by 91 days.

(21) Appl. No.: 13/189,640

(22) Filed: Jul. 25, 2011

(65) Prior Publication Data
US 2012/0029029 A1 Feb. 2, 2012

Related U.S. Application Data

(60) Provisional application No. 61/368,099, filed on Jul. 27, 2010.

(51) Int. Cl.
A61K 31/426 (2006.01)
A61K 31/427 (2006.01)
A61K 31/4439 (2006.01)
C07D 277/42 (2006.01)
C07D 417/12 (2006.01)

(52) U.S. Cl.
USPC ......... 548/194; 546/270.7; 514/342; 514/370

(58) Field of Classification Search
USPC ..................................... 548/194; 546/270.7
See application file for complete search history.

(56) References Cited

U.S. PATENT DOCUMENTS

| | | | |
|---|---|---|---|
| 4,851,423 A | 7/1989 | Girijavallabhan et al. |
| 5,258,407 A | 11/1993 | Washburn et al. |
| 5,272,167 A | 12/1993 | Girijavallabhan et al. |
| 5,459,144 A | 10/1995 | Girijavallabhan et al. |
| 5,596,020 A | 1/1997 | Morris et al. |
| 5,750,532 A | 5/1998 | Girijavallabhan et al. |
| 5,786,379 A | 7/1998 | Bernardon |
| 6,001,879 A | 12/1999 | Seitz et al. |
| 6,458,803 B1 | 10/2002 | Sikorski et al. |
| 6,506,783 B1 | 1/2003 | Camden |
| 6,521,641 B1 | 2/2003 | Klein et al. |
| 6,548,549 B1 | 4/2003 | Seitz et al. |
| 6,833,371 B2 | 12/2004 | Atkinson et al. |
| 7,132,436 B2 | 11/2006 | Kurz et al. |
| 7,358,238 B2 | 4/2008 | Andersen et al. |
| 7,501,405 B2 | 3/2009 | Kampen et al. |
| 7,645,773 B2 | 1/2010 | Gillespie et al. |
| 7,700,583 B2 | 4/2010 | Gundertofte et al. |
| 7,723,323 B2 | 5/2010 | Andersen et al. |
| 8,048,908 B2 | 11/2011 | Ebdrup et al. |
| 8,053,431 B2 | 11/2011 | Kilburn et al. |
| 8,053,447 B2 | 11/2011 | Ebdrup et al. |
| 8,138,342 B2 | 3/2012 | Kilburn et al. |
| 8,153,798 B2 | 4/2012 | Kilburn et al. |
| 2005/0154202 A1 | 7/2005 | Hagmann et al. |
| 2005/0250776 A1 | 11/2005 | Barf et al. |
| 2005/0261302 A1 | 11/2005 | Hoff et al. |
| 2006/0079506 A1 | 4/2006 | Linders et al. |
| 2006/0094699 A1 | 5/2006 | Kampen et al. |
| 2006/0111366 A1 | 5/2006 | Andersen et al. |
| 2006/0149070 A1 | 7/2006 | Rohde et al. |
| 2006/0281773 A1 | 12/2006 | Patel et al. |
| 2007/0270408 A1 | 11/2007 | Andersen et al. |
| 2008/0108598 A1 | 5/2008 | Andersen et al. |
| 2009/0124598 A1 | 5/2009 | Andersen et al. |
| 2009/0137574 A1 | 5/2009 | Kampen et al. |
| 2009/0264412 A1 | 10/2009 | Kampen et al. |
| 2009/0264414 A1 | 10/2009 | Andersen et al. |
| 2009/0306048 A1 | 12/2009 | Kilburn et al. |
| 2009/0325932 A1 | 12/2009 | Ebdrup et al. |
| 2010/0056600 A1 | 3/2010 | Ebdrup et al. |
| 2010/0087543 A1 | 4/2010 | Ebdrup et al. |
| 2010/0120743 A1 | 5/2010 | Gundertofte et al. |
| 2010/0137377 A1 | 6/2010 | Petersen et al. |
| 2010/0168083 A1 | 7/2010 | Ebdrup |
| 2010/0197658 A1 | 8/2010 | Andersen et al. |
| 2010/0331366 A1 | 12/2010 | Ebdrup |
| 2011/0003852 A1 | 1/2011 | Ebdrup |
| 2011/0003856 A1 | 1/2011 | Ebdrup |
| 2011/0039853 A1 | 2/2011 | Ebdrup |
| 2011/0224244 A1 | 9/2011 | Polisetti et al. |
| 2011/0312949 A1 | 12/2011 | Kilburn et al. |
| 2012/0004209 A1 | 1/2012 | Ebdrup et al. |
| 2012/0010194 A1 | 1/2012 | Ebdrup et al. |

FOREIGN PATENT DOCUMENTS

| | | |
|---|---|---|
| WO | WO 97/07789 | 3/1997 |
| WO | WO 97/22588 | 6/1997 |
| WO | WO 97/24328 | 7/1997 |
| WO | WO 00/73283 | 12/2000 |

(Continued)

OTHER PUBLICATIONS

Andrew et al., J. Clin. Endocrinol. Metab. vol. 87, pp. 277-285 (2002).

(Continued)

*Primary Examiner* — Laura L. Stockton
(74) *Attorney, Agent, or Firm* — Samuel B. Rollins

(57) ABSTRACT

The present invention is directed to substituted thiazol-2-ylamine derivatives and pharmaceutically acceptable salts thereof that inhibit 11βHSD1 and that may be useful in the treatment of diseases in which modulation or inhibition of 11βHSD1 is beneficial or where a reduction in intracellular glucorticoid levels is desirable. The invention is also directed to pharmaceutical compositions comprising these compounds and the use of these compounds and compositions in the treatment of such diseases, disorders, or conditions in which modulation or inhibition of 11βHSD1 is beneficial or where a reduction in intracellular glucorticoid levels is desirable.

41 Claims, No Drawings

(56) References Cited

FOREIGN PATENT DOCUMENTS

| WO | WO 01/90090 | 11/2001 |
|---|---|---|
| WO | WO 01/90091 | 11/2001 |
| WO | WO 01/90092 | 11/2001 |
| WO | WO 01/90093 | 11/2001 |
| WO | WO 01/90094 | 11/2001 |
| WO | WO 02/02797 | 1/2002 |
| WO | WO 02/072084 | 9/2002 |
| WO | WO 02/076435 | 10/2002 |
| WO | WO 03/065983 | 8/2003 |
| WO | WO 03/070732 | 8/2003 |
| WO | WO 03/086410 | 10/2003 |
| WO | WO 2004/033427 | 4/2004 |
| WO | WO 2004/052461 | 6/2004 |
| WO | WO 2004/056744 | 7/2004 |
| WO | WO 2004/056745 | 7/2004 |
| WO | WO 2006/044645 | 7/2004 |
| WO | WO 2004/065351 | 8/2004 |
| WO | WO 2004/087159 | 10/2004 |
| WO | WO 2004/089380 | 10/2004 |
| WO | WO 2004/089415 | 10/2004 |
| WO | WO 2004/089416 | 10/2004 |
| WO | WO 2004/089470 | 10/2004 |
| WO | WO 2004/089471 | 10/2004 |
| WO | WO 2004/089896 | 10/2004 |
| WO | WO 2005/013950 | 2/2005 |
| WO | WO 2005/085202 | 9/2005 |
| WO | WO 2006/014012 | 2/2006 |
| WO | WO 2006/028958 | 3/2006 |
| WO | WO 2006/040329 | 4/2006 |
| WO | WO 2006/048330 | 5/2006 |
| WO | WO 2006/055752 | 5/2006 |
| WO | WO 2006/094633 | 9/2006 |
| WO | WO 2006/105127 | 10/2006 |
| WO | WO 2006/113261 | 10/2006 |
| WO | WO 2007/051810 | 5/2007 |
| WO | WO 2007/051811 | 5/2007 |
| WO | WO 2007/058960 | 5/2007 |
| WO | WO 2007/066784 | 6/2007 |
| WO | WO 2007/107550 | 9/2007 |
| WO | WO 2007/115935 | 10/2007 |
| WO | WO 2007/144394 | 12/2007 |
| WO | WO 2008/006702 | 1/2008 |
| WO | WO 2008/006703 | 1/2008 |
| WO | WO 2008/101885 | 8/2008 |
| WO | WO 2008/101886 | 8/2008 |
| WO | WO 2008/101907 | 8/2008 |
| WO | WO 2008/101914 | 8/2008 |
| WO | WO 2008/110196 | 9/2008 |
| WO | WO 2008/119017 | 10/2008 |
| WO | WO 2008/127924 | 10/2008 |
| WO | WO 2008/134221 | 11/2008 |
| WO | WO 2009/126863 | 10/2009 |
| WO | WO 2010/057126 | 5/2010 |
| WO | WO 2010/059618 | 5/2010 |

OTHER PUBLICATIONS

Andrews et al., J. Clin. Endocrinol. Metab. vol. 88, pp. 285-291 (2003).
Barf T et al: "Recent progress in 11-[beta]-hydroxysteroid dehydrogenase type 1 (11-[beta]-HSD1) inhibitor development" Drugs of the Future 2006 Spain, vol. 31, No. 3, Mar. 2006, pp. 231-243.
Bird et al., J. Physiology vol. 585, pp. 187-201 (2007).
Brem et al., Hypertension vol. 31, pp. 459-462 (1998).
Brindley et al., Progress Lipid Res. vol. 30, pp. 349-360 (1991).
Bujalska et al., Endocrinology vol. 140, pp. 3188-3196 (1999).
Cooper et al., Bone vol. 27, pp. 375-381 (2000).
Coppola, Gary M. et al., "Perhydroquinolylbenzamides as Novel Inhibitors of 11.beta.-Hydroxysteroid Dehydrogenase Type 1" Journal of Medicinal Chemistry, 48 (21), 6696-6712 Coden: Jmcmar; ISSN: 0022-2623, 2005.
Davani et al., J. Biol. Chem. vol. 275, pp. 34841-34844 (2000).
Evans et al., J. Med. Chem. vol. 35, pp. 3919-3927 (1992).
Fotsch C. et al., "11[beta]-Hydroxysteroid dehydrogenase-1 as a therapeutic target for metabolic diseases" Expert Opinion on Therapeutic Patents, Ashley Publications, GB, vol. 15, No. 3, 2005, pp. 289-303.
Hosfield et al., J. Biol. Chem. vol. 280, pp. 4639-4648 (2005).
Ignatova et al., American Journal of Physiology—Endocrinology and Metabolism, 296(2):E367-E377 (2009).
International Search Report and Written Opinion for related International Application No. PCT/US2011/045141 mailed Dec. 12, 2011.
Johnson et al., J. Org. Chem. vol. 35, pp. 622-626 (1970).
Koteletseve et al., Proc. Nat'l Acad. Sci. vol. 94, pp. 14924-14929 (1997).
Masuzaki et al., J. Clin. Invest. vol. 112, pp. 83-90 (2003).
Masuzaki et al., Science vol. 294, pp. 2166-2170 (2001).
Moisan et al., Endocrinology, vol. 127, pp. 1450-1455 (1990).
Morton et al., J. Biol. Chem. vol. 276, pp. 41293-41300 (2001).
Nankervis et al.: "Calcium sensitizazion as a positive inotropic mechanism. . ." Journal of Cardiovascular Pharmacology, vol. 24, No. 4, 1994, pp. 612-617.
Rauz et al., Invest. Opthalmol. Vis. Sci. vol. 42, pp. 2037-2042 (2001).
Reed et al., Scand J. Gastroentreol. vol. 15, pp. 51-56 (1980).
Restriction Requirement dated Jan. 27, 2012 for U.S. Appl. No. 12/595,310.
Schwartz et al., Nature vol. 404, pp. 661-671 (2000).
Souness et al., Steroids vol. 67, pp. 195-201 (2002).
Tannin et al., J. Biol. Chem. vol. 266, pp. 16653-16658 (1991).
Tomlinson et al., J. Clin. Endocrinol. Metab. vol. 87, pp. 57-62 (2002).
Walker et al., J. Clin. Endocrinol. Metab. vol. 80, pp. 3155-3159 (1995).
Whitworth et al., J. Hypertens. vol. 20, pp. 1035-1043 (2002).
Whorwood et al., J. Clin. Endocrinol. Metab. vol. 86, pp. 2296-2308 (2001).
Yau et al., Proc. Nat'l Acad. Sci. vol. 98, pp. 4716-4721 (2001).
Yudt et al., Mol. Endocrinol. vol. 16, pp. 1719-1726 (2002).
Office Action for U.S. Appl. No. 13/128,045 dated Sep. 26, 2012.
Rauz et al., "Inhibition of 11beta-hydroxysteroid dehydrogenase type 1 lowers intraocular pressure in patients with ocular hypertension" Q. J. Med., 96:481-490 (2003).
Tomlinson, et al., "11beta-Hydroxysteroid Dehydrogenase Type 1: A Tissue-Specific Regulator of Glucocorticoid Response," Endocrine Reviews, 25(5):831-866 (2004).
International Preliminary Report on Patentability and Written Opinion for related International Application No. PCT/US2011/045141 mailed Feb. 7, 2013.

SUBSTITUTED THIAZOL-2-YLAMINE DERIVATIVES, PHARMACEUTICAL COMPOSITIONS, AND METHODS OF USE AS 11-BETA HSD1 MODULATORS

CROSS-REFERENCE TO RELATED APPLICATIONS

This application claims the benefit of priority of U.S. Provisional Patent Application No. 61/368,099, filed Jul. 27, 2010.

FIELD OF INVENTION

The invention provides substituted thiazol-2-ylamine derivatives that may be useful as compounds that modulate the activity of 11-beta hydroxysteroid dehydrogenase type 1 (11βHSD1), and that may therefore serve as treatments for diseases, disorders, or conditions where modulation of 11βHSD1 is beneficial.

DESCRIPTION OF RELATED ART

Metabolic syndrome is a major global health problem. In the United States, for example, the prevalence of metabolic syndrome in the adult population may be as high as 25%. Metabolic syndrome is characterized by some combination of insulin resistance, dyslipidemia, obesity, and hypertension, which leads to an increased risk of mortality due to various cardiovascular diseases. Furthermore, persons with metabolic syndrome are at increased risk of developing type 2 diabetes, whose prevalence is escalating worldwide.

In the clinical setting, it is known that glucocorticoids are able to induce most of the cardinal features of metabolic syndrome and type 2 diabetes.

11βHSD1 catalyzes the local generation of active glucocorticoid in several tissues and organs, especially in the liver and in adipose tissue, but also to a lesser extent in skeletal muscle, bone, the pancreas, the endothelium, ocular tissue, and in certain parts of the central nervous system. Thus, 11βHSD1 can serve as a local regulator of glucocorticoid action in the tissues and organs where it is expressed.

The role of 11βHSD1 in metabolic syndrome and type 2 diabetes is supported by several lines of evidence. In humans, treatment with the non-specific 11βHSD1 inhibitor carbenoxolone improves insulin sensitivity in lean healthy individuals and in persons with type 2 diabetes. In addition, 11βHSD1 knock-out mice are resistant to insulin resistance induced by obesity and stress. The knock-out mice exhibit an anti-atherogenic lipid profile of decreased VLDL triglycerides and increased HDL-cholesterol. Mice that overexpress 11βHSD1 in adipocytes develop insulin resistance, hyperlipidemia, and visceral obesity, a phenotype that resembles the human metabolic syndrome.

The more mechanistic aspects of 11βHSD1 modulation, and thereby modulation of intracellular levels of active glucocorticoid, have been investigated in several rodent models and in different cellular systems. 11βHSD1 promotes the features of metabolic syndrome by increasing hepatic expression of the rate-limiting enzymes in gluconeogenesis, namely phosphoenolpyuvate carboxykinase and glucose-6-phosphatase, thereby promoting differentiation of preadipocytes into adipocytes, which facilitates obesity, directly and indirectly stimulates hepatic VLDL secretion, decreases hepatic LDL uptake, and increases vessel contractility.

WO 2001/090090, WO 2001/090091, WO 2001/090092, WO 2001/090093, and WO 2001/090094 describe various compounds that may inhibit the activity of 11βHSD1 and that are alleged to be useful in treating diabetes, obesity, glaucoma, osteoporosis, cognitive disorders, immune disorders, and depression. WO 2004/089470 describes various compounds that may stimulate the activity of 11βHSD1. WO 2004/089415 and WO 2004/089416 describe various combinations 11βHSD1 inhibitors with other therapeutically active compounds, such as glucocorticoid receptor agonists and antihypertensive agents.

Nevertheless, there is a continuing need for new compounds that may modulate the activity of 11βHSD1 and thereby alter intracellular concentrations of active glucocorticoid. In particular, there is a continuing need for new compounds that may inhibit the activity of 11βHSD1, thereby leading to decreased intracellular concentrations of active glucocorticoid. Such compounds may be useful as potential treatments for disorders where a decreased level of active intracellular glucocorticoid is desirable, such as metabolic syndrome, type 2 diabetes, impaired glucose tolerance (IGT), impaired fasting glucose (IFG), dyslipidemia, obesity, hypertension, diabetic late complications, cardiovascular diseases, arteriosclerosis, atherosclerosis, myopathy, muscle wasting, osteoporosis, neurodegenerative and psychiatric disorders, glaucoma, and the adverse effects of treatment or therapy with glucocorticoid receptor agonists.

SUMMARY OF THE INVENTION

The invention provides substituted thiazol-2-ylamine derivatives that modulate the activity of 11βHSD1 and that therefore may be useful in the treatment of diseases, disorders, or conditions where modulation of 11βHSD1 is beneficial, such as metabolic syndrome, type 2 diabetes, impaired glucose tolerance (IGT), impaired fasting glucose (IFG), dyslipidemia, obesity, hypertension, diabetic late complications, cardiovascular diseases, arteriosclerosis, atherosclerosis, myopathy, muscle wasting, osteoporosis, neurodegenerative and psychiatric disorders, adverse effects of treatment or therapy with glucocorticoid receptor agonists, and the dysregulation of intraocular pressure, including glaucoma. The invention also provides pharmaceutical compositions comprising a substituted thiazol-2-ylamine derivative, and for the use of such compounds and/or compositions in treating one or more of the above diseases, disorders, or conditions.

In one aspect, the invention provides compounds of Formula (I) and pharmaceutically acceptable salts thereof, where the identity of individual substituents is set forth in greater detail below.

In another aspect, the present invention provides methods for the preparation of compounds of Formula (I) and pharmaceutically acceptable salts thereof.

In another aspect, the invention provides pharmaceutical compositions comprising a compound of Formula (I) or a pharmaceutically acceptable salt thereof. In one embodiment, the pharmaceutical composition comprises a compound of Formula (I) or a pharmaceutically acceptable salt thereof, and a pharmaceutically acceptable carrier, excipient, or diluent.

In another aspect, the present invention provides a method for the preparation of a pharmaceutical composition comprising a compound of Formula (I) or a pharmaceutically acceptable salt thereof.

In another aspect, the present invention provides methods of treatment comprising administering a compound of Formula (I) or a pharmaceutically acceptable salt thereof, or a pharmaceutical composition comprising a compound of Formula (I) or a pharmaceutically acceptable salt thereof, to a subject who has a disease, disorder, or condition.

In another aspect, the present invention provides methods of treatment comprising administering a compound of Formula (I) or a pharmaceutically acceptable salt thereof, or a pharmaceutical composition comprising a compound of Formula (I) or a pharmaceutically acceptable salt thereof, to a subject having a disease, disorder, or condition or a subject at risk for having a disease, disorder, or condition, wherein the disease, disorder, or condition is selected from the group consisting of: metabolic syndrome, type 2 diabetes, impaired glucose tolerance (IGT), impaired fasting glucose (IFG), dyslipidemia, obesity, hypertension, diabetic late complications, cardiovascular diseases, arteriosclerosis, atherosclerosis, myopathy, muscle wasting, osteoporosis, neurodegenerative and psychiatric disorders, adverse effects of treatment or therapy with glucocorticoid receptor agonists, and dysregulation of intraocular pressure including glaucoma.

Additional features of the present invention are described hereinafter.

BRIEF DESCRIPTION OF DRAWINGS

Not applicable.

DETAILED DESCRIPTION

The following definitions are meant to clarify the terms defined. If a particular term used herein is not specifically defined, the term should not be considered to be indefinite. Rather, such undefined terms are to be construed in accordance with their plain and ordinary meaning to skilled artisans in a field of art to which the invention is directed.

As used herein the term "alkyl" refers to a fully saturated straight or branched chain hydrocarbon having one to ten carbon atoms, which may be optionally substituted, as herein further described, with multiple degrees of substitution being allowed. Examples of "alkyl" include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl.

The number carbon atoms in an alkyl group will be represented by the phrase "$C_{x-y}$ alkyl," which refers to an alkyl group, as herein defined, containing from x to y, inclusive, carbon atoms. Thus, $C_{1-6}$ alkyl represents an alkyl chain having from 1 to 6 carbons as described above, and for example, includes, but is not limited to, methyl, ethyl, n-propyl, isopropyl, isobutyl, n-butyl, sec-butyl, tert-butyl, isopentyl, n-pentyl, neopentyl, and n-hexyl.

As used herein, the term "alkylene" refers to a fully saturated straight or branched chain divalent hydrocarbon radical having from one to ten carbon atoms, which may be optionally substituted as herein further described, with multiple degrees of substitution being allowed. Examples of "alkylene" include, but are not limited to, methylene, ethylene, n-propylene, 1-methylethylene, 2-methylethylene, dimethylmethylene, n-butylene, 1-methyl-n-propylene, and 2-methyl-n-propylene.

The number of carbon atoms in an alkylene group will be represented by the phrase "$C_{x-y}$ alkylene," which refers to an alkylene group, as herein defined, containing from x to y, inclusive, carbon atoms. Thus, $C_{1-4}$ alkylene represents an alkylene chain having from 1 to 4 carbons as described above, and for example, includes, but is not limited to, methylene, ethylene, n-propylene, 1-methylethylene, 2-methylethylene, dimethylmethylene, n-butylene, 1-methyl-n-propylene, and 2-methyl-n-propylene.

As used herein, the term "halogen" refers to fluorine, chlorine, bromine, or iodine.

As used herein, the term "aryl" refers to a six- to ten-membered cyclic, aromatic hydrocarbon, which may be optionally substituted as herein further described, with multiple degrees of substitution being allowed. Examples of "aryl" groups as used herein include, but are not limited to, phenyl and naphthyl. As used herein, the term "aryl" also includes ring systems in which a phenyl or naphthyl group is optionally fused with one to three non-aromatic, saturated or unsaturated, carbocyclic rings. For example, "aryl" would include ring systems such as indene, with attachment possible to either the aromatic or the non-aromatic ring(s).

As used herein, the term "heteroaryl" refers to a five- to fourteen-membered optionally substituted mono- or polycyclic ring system, which contains at least one aromatic ring and also contains one or more heteroatoms. Such "heteroaryl" groups may be optionally substituted as herein further described, with multiple degrees of substitution being allowed. In a polycyclic "heteroaryl" group that contains at least one aromatic ring and at least one non-aromatic ring, the aromatic ring(s) need not contain a heteroatom. Thus, for example, "heteroaryl," as used herein, would include indolinyl. Further, the point of attachment may be to any ring within the ring system without regard to whether the ring containing the attachment point is aromatic or contains a heteroatom. Thus, for example, "heteroaryl," as used herein, would include indolin-1-yl, indolin-3-yl, and indolin-5-yl. Examples of heteroatoms include nitrogen, oxygen, or sulfur atoms, including N-oxides, sulfur oxides, and sulfur dioxides, where feasible. Examples of "heteroaryl" groups include, but are not limited to, furyl, thiophenyl, pyrrolyl, oxazolyl, thiazolyl, imidazolyl, isoxazolyl, isothiazolyl, 1,2,4-triazolyl, pyrazolyl, pyridinyl, pyridazinyl, pyrimidinyl, indolyl, isoindolyl, benzo[b]thiophenyl, benzimidazolyl, benzothiazolyl, pteridinyl, and phenazinyl, where attachment can occur at any point on said rings, as long as attachment is chemically feasible. Thus, for example, "thiazolyl" refers to thiazol-2-yl, thiazol-4-yl, and thiaz-5-yl.

As used herein, when "heteroaryl" is recited as a possible substituent, the "heteroaryl" group can attach through either a carbon atom or any heteroatom, to the extent that attachment at that point is chemically feasible.

As used herein, the term "substituted" refers to substitution of one or more hydrogens of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

As used herein, the various functional groups represented will be understood to have a point of attachment at the functional group having the hyphen or dash (-) or an asterisk (*). In other words, in the case of —CH$_2$CH$_2$CH$_3$, it will be understood that the point of attachment is the CH$_2$ group at the far left. If a substituent group is recited without an asterisk or a dash, then its attachment point is the attachment point that skilled artisans would generally associate with that group. For example, "methyl" is —CH$_3$, as that conforms to the generally understood meaning of what a methyl group is.

When any variable occurs more than one time in any one constituent, or multiple constituents, its definition on each occurrence is independent of its definition on every other occurrence.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

As used herein, the term "optionally" means that the subsequently described event(s) may or may not occur.

As used herein, "administer" or "administering" means to introduce, such as to introduce to a subject a compound or composition. The term is not limited to any specific mode of delivery, and can include, for example, subcutaneous delivery, intravenous delivery, intramuscular delivery, intracisternal delivery, delivery by infusion techniques, transdermal delivery, oral delivery, nasal delivery, and rectal delivery. Furthermore, depending on the mode of delivery, the administering can be carried out by various individuals, including, for example, a health-care professional (e.g., physician, nurse, etc.), a pharmacist, or the subject (i.e., self-administration).

As used herein, "treat" or "treating" or "treatment" can refer to one or more of: delaying the progress of a disease, disorder, or condition; controlling a disease, disorder, or condition; ameliorating one or more symptoms characteristic of a disease, disorder, or condition; or delaying the recurrence of a disease, disorder, or condition, or characteristic symptoms thereof, depending on the nature of the disease, disorder, or condition and its characteristic symptoms.

As used herein, "subject" refers to any mammal such as, but not limited to, humans, horses, cows, sheep, pigs, mice, rats, dogs, cats, and primates such as chimpanzees, gorillas, and rhesus monkeys. In an embodiment, the "subject" is a human. In another embodiment, the "subject" is a human who exhibits one or more symptoms characteristic of a disease, disorder, or condition. The term "subject" does not require one to have any particular status with respect to a hospital, clinic, or research facility (e.g., as an admitted patient, a study participant, or the like).

As used herein, the term "compound" includes free acids, free bases, and salts thereof. Thus, phrases such as "the compound of embodiment 1" or "the compound of claim 1" are intended to refer to any free acids, free bases, and salts thereof that are encompassed by embodiment 1 or claim 1.

As used herein, "substituted thiazol-2-ylamine derivatives" refers to compounds represented by Formula (I) or pharmaceutically acceptable salts thereof, as described in detail below.

As used herein, the term "pharmaceutical composition" is used to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

Also included within the scope of the invention are the individual enantiomers of the compounds represented by Formula (I) or pharmaceutically acceptable salts thereof, as well as any wholly or partially racemic mixtures thereof. The invention also covers the individual enantiomers of the compounds represented by Formula (I) or pharmaceutically acceptable salts thereof, as well as mixtures with diastereoisomers thereof in which one or more stereocenters are inverted. Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

In several aspects, the present invention relates to substituted thiazol-2-ylamine derivatives, pharmaceutical compositions comprising a substituted thiazol-2-ylamine derivative, methods of making a substituted thiazol-2-ylamine derivative, methods of making pharmaceutical compositions comprising a substituted thiazol-2-ylamine derivative, and methods of using a substituted thiazol-2-ylamine derivative or pharmaceutical compositions comprising a substituted thiazol-2-ylamine derivative, particularly for the treatment of diseases, disorders, or conditions where modulation of 11βHSD1 is beneficial, such as metabolic syndrome, type 2 diabetes, impaired glucose tolerance (IGT), impaired fasting glucose (IFG), dyslipidemia, obesity, hypertension, diabetic late complications, cardiovascular diseases, arteriosclerosis, atherosclerosis, myopathy, muscle wasting, osteoporosis, neurodegenerative and psychiatric disorders, adverse effects of treatment or therapy with glucocorticoid receptor agonists, and dysregulation of intraocular pressure including glaucoma.

In a first aspect, the present invention provides a substituted thiazol-2-ylamine derivative or a pharmaceutically acceptable salt thereof. Such compounds are useful in modulating the activity of 11βHSD1, as discussed in more detail below.

In a first embodiment (i.e., embodiment 1), the invention provides a compound of Formula (I) or a pharmaceutically acceptable salt thereof:

wherein
R$^1$ is 5-hydroxy-adamant-2-yl;
A$^1$ is

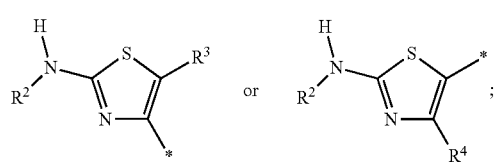

and

R² is aryl, heteroaryl, —C₁₋₄ alkylene-aryl, or —C₁₋₄ alkylene-heteroaryl, where the aryl and heteroaryl groups are optionally substituted one or more times with substituents selected independently from the group consisting of halogen, C₁₋₄ alkyl, —O—C₁₋₄ alkyl, —CF₃, —CH₂CF₃, —CF₂CF₃, and —OCF₃;

R³ and R⁴ are each independently selected from the group consisting of hydrogen, halogen, C₁₋₄ alkyl, —O—C₁₋₄ alkyl, —CF₃, —CH₂CF₃, —CF₂CF₃, and —OCF₃.

Embodiment 2: A compound according to embodiment 1, wherein

R² is phenyl optionally substituted one or more times with substituents selected independently from the group consisting of halogen, C₁₋₄ alkyl, —O—C₁₋₄ alkyl, —CF₃, —CH₂CF₃, —CF₂CF₃, and —OCF₃.

Embodiment 3: A compound according to embodiment 2, wherein

R² is phenyl optionally substituted one or two times with substituents selected independently from the group consisting of fluoro, chloro, methoxy, trifluoromethyl, and trifluoromethoxy.

Embodiment 4: A compound according to embodiment 3, wherein

R² is phenyl optionally substituted once with fluoro, chloro, methoxy, or trifluoromethyl.

Embodiment 5: A compound according to embodiment 3, wherein

R² is phenyl optionally substituted twice with chloro.

Embodiment 6: A compound according to embodiment 1, wherein

R² is 2-pyridyl, 3-pyridyl, or 4-pyridyl optionally substituted one or more times with substituents selected independently from the group consisting of halogen, C₁₋₄ alkyl, —O—C₁₋₄ alkyl, —CF₃, —CH₂CF₃, —CF₂CF₃, and —OCF₃.

Embodiment 7: A compound according to embodiment 6, wherein

R² is 2-pyridyl, 3-pyridyl, or 4-pyridyl substituted one or two times with chloro.

Embodiment 8: A compound according to embodiment 6, wherein

R² is 2-pyridyl, 3-pyridyl, or 4-pyridyl, each of which is unsubstituted.

Embodiment 9: A compound according to embodiment 1, wherein

R² is phenethyl or benzyl.

Embodiment 10: A compound according to embodiment 1, wherein

R² is —CH₂-(2-furyl).

Embodiment 11: A compound according to embodiment 1, wherein

R² is —CH₂CH₂-(2-pyridyl); —CH₂CH₂-(3-pyridyl); or —CH₂CH₂-(4-pyridyl).

Embodiment 12: A compound according to embodiment 1, wherein

R² is —CH₂-(3-pyridyl).

Embodiment 13: A compound according to embodiment 1, wherein

R² is phenyl optionally substituted one or more times with substituents selected independently from the group consisting of halogen, C₁₋₄ alkyl, —O—C₁₋₄ alkyl, —CF₃, —CH₂CF₃, —CF₂CF₃, and —OCF₃; or R² is 2-pyridyl, 3-pyridyl, or 4-pyridyl optionally substituted one or more times with substituents selected independently from the group consisting of halogen, C₁₋₄ alkyl, —O—C₁₋₄ alkyl, —CF₃, —CH₂CF₃, —CF₂CF₃, and —OCF₃; or R² is phenethyl or benzyl; or R² is —CH₂-(2-furyl); or R² is —CH₂CH₂-(2-pyridyl); —CH₂CH₂-(3-pyridyl); or —CH₂CH₂-(4-pyridyl); or R² is —CH₂-(3-pyridyl).

Embodiment 14: A compound according to any one of embodiments 1 to 13, wherein

A¹ is

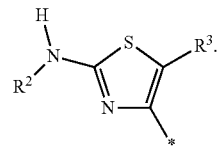

Embodiment 15: A compound according to any one of embodiments 1 to 13, wherein

A¹ is

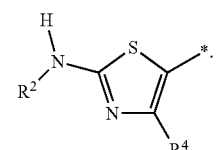

Embodiment 16: A compound according to any one of embodiments 1 to 15, wherein

R³ and R⁴ are hydrogen.

Embodiment 17: A compound according to any one of embodiments 1 to 15, wherein

R³ and R⁴ are independently hydrogen or methyl.

Embodiment 18: A compound according to any one of embodiments 1 to 17, wherein the bond between the 5-hydroxy-adamant-2-yl group of R¹ and the adjacent N atom in Figure (I) is an equatorial connection with respect to the adamantane ring.

Embodiment 19: A compound according to any one of embodiments 1 to 18, wherein the substitutions at the 2 and 5 positions of the 5-hydroxy-adamant-2-yl group of R¹ are entgegen (E) (trans) to each other.

Embodiment 20: A compound according to any one of embodiments 1 to 19, wherein the compound exists in the form of a free base.

Embodiment 21: A compound according to any one of embodiments 1 to 19, wherein the compound exists in the form of a pharmaceutically acceptable salt.

Embodiment 22: A compound according to embodiment 21, wherein the compound exists in the form of a hydrochloride salt.

General Experimental Section

The routes below illustrate general methods of synthesizing compounds of Formula (I) and/or pharmaceutically acceptable salts thereof. The skilled artisan will appreciate that the compounds of the invention could be made by methods other than those specifically described herein, by adaptation of the methods described herein and/or by adaptation of methods known in the art. In general, compounds of the invention may be prepared in a multi-step synthesis, as shown below. All quantities shown are approximate, and are given solely for illustrative purposes.

The following abbreviations may be used in describing reaction conditions, common reagents, common solvents, or methods of analysis.

DIEA=diisopropylethylamine
HBTU=2-(1H-benzotriazol-1-yl)-1,1,3,3-tetramethyluronium hexafluorophosphate
LCMS=LC-MS=LC/MS=liquid chromatography-mass spectrometry analysis
THF=tetrahydrofuran
Fmoc-NCS=fluorenylmethyloxycarbonyl isothiocyanate
TLC=thin layer chromatography
rt or RT=room temperature
h=hour
min=minutes
M=molar concentration
N=normal concentration General Procedure A: Preparation of a Thiourea from an Amine A solution of an amine (1 mmol) in either dichloromethane (10 mL) or a 1:1 mixture of dichloromethane and tetrahydrofuran (10 mL) is charged with Fmoc-NCS (1.05 mmol). The reaction is stirred at room temperature or at reflux and is allowed to go to completion in about 4 hours, as indicated by LC-MS analysis. To the same reaction mixture, piperidine (3 mmol) is added, and the resulting mixture is stirred at room temperature for about 8 hours. A precipitate forms and is then filtered and washed with hexanes:ethyl acetate (9:1, 100 mL) to yield a thiourea.

General Procedure B: Preparation of a Thiazole from a Thiourea

A solution of a thiourea (1 mmol) in methanol (3 mL) is charged with either 3-bromo-2-oxo-propionic acid ethyl ester (1.05 mmol) or 3-bromo-2-oxo-propionic acid (1.05 mmol). The reaction mixture is stirred at room temperature and is allowed to proceed to completion in about 1-2 hours, as indicated by LC-MS analysis. The resulting product is concentrated and dried to yield a crude ester or acid that can be used in an additional reaction without further purification.

General Procedure C: Preparation of a Thiazole from a Thiourea

A solution of a thiourea (1 mmol) in methanol (2 mL) is charged with 3-bromo-2-oxo-propionic acid ethyl ester (1.1 mmol). The reaction is stirred at room temperature and allowed to go to completion in about 1-2 hours, as indicated by LC-MS analysis. The reaction product is then concentrated and dried to yield a crude ester or acid. The crude product is hydrolyzed using a 1:1:1 mixture of methanol, tetrahydrofuran, and 2N NaOH aqueous (1.5 ml) at room temperature for about 3 hours. The reaction product is then concentrated, and the aqueous layer is acidified to pH 4.0 and the product is partitioned between water and ethyl acetate (1:1). The organic phase is then dried over $Na_2SO_4$, concentrated, and the crude acid may be used in an additional reaction without further purification.

General Procedure D: Preparation of an Amide from a Carboxylic Acid

To a solution of a carboxylic acid (1 mmol) in dimethylformamide (2 mL) are added DIEA (3.0 mmol), HBTU (1.1 mmol), and amine (1.1 mmol). The reaction mixture is stirred at room temperature and is allowed to go to completion in about 8 hours, as indicated by LC-MS analysis. The reaction product is partitioned between water and ethyl acetate (1:1). The organic phase is dried over $Na_2SO_4$, concentrated, and the residue is purified by automated flash chromatography on a pre-packed silica (12 g) column using hexanes:ethyl acetate or dichloromethane:methanol as the eluent, so as to yield an amide.

Example Compounds

Examples of compounds of Formula (I) or pharmaceutically acceptable salts thereof are described below, including procedures used for synthesizing the compounds. Each of the identified compounds constitutes a separate embodiment of the invention, where the embodiments include the compound in its free (non-salted) form and pharmaceutically acceptable salts of the free compound. Each of the recited compounds in its free (non-salted) form constitutes a separate embodiment of the invention. In addition, the pharmaceutically acceptable salts of each of the recited compounds constitute a separate embodiment of the invention. In other embodiments, the hydrochloride salts of each of the recited compounds constitute a separate embodiment of the invention. LC-MS data are provided for each compound. The recorded m/z data are accurate to within about 1 amu. For some examples, proton NMR spectra were also recorded, although such data are not shown.

Example 1

2-[(Furan-2-ylmethyl)-amino]-thiazole-4-carboxylic acid [(E)-5-hydroxy-adamantan-2-yl]-amide

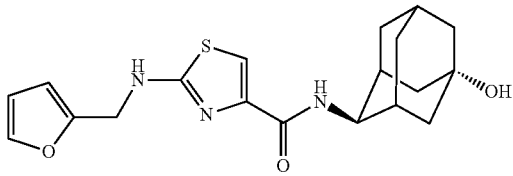 [SMILES: O=C(N[C@H]1C2CC3CC1C[C@](O)(C3)C2)c1csc(NCc2ccco2)n1]

2-[(Furan-2-ylmethyl)-amino]-thiazole-4-carboxylic acid (220 mg) was prepared according to General Procedure B using furan-2-ylmethyl-thiourea (156 mg) and 3-bromo-2-oxo-propionic acid (167 mg).

2-[(Furan-2-ylmethyl)-amino]-thiazole-4-carboxylic acid [(E)-5-hydroxy-adamantan-2-yl]-amide (105 mg) was prepared from 2-[(furan-2-ylmethyl)-amino]-thiazole-4-carboxylic acid (100 mg), and (E)-4-amino-adamantan-1-ol hydrochloride (100 mg) in dimethylformamide (2 mL) according to General Procedure D. The crude product was purified by automated flash chromatography on a prepacked silica (12 g) column using hexanes:ethyl acetate as the eluent, so as to yield the title compound.

LC-MS (m/z): 373.79 (M+1)$^+$; $^1$H NMR (400 MHz, DMSO-d$_6$): δ 8.27-8.31 (m, 1H), 7.58-7.60 (m, 1H), 7.52-7.56 (m, 1H), 7.24-7.26 (m, 1H), 6.39-6.42 (m, 1H), 6.31-6.34 (m, 1H), 4.44-4.47 (m, 2H), 3.87-3.92 (m, 1H), 1.98-2.08 (m, 3H), 1.62-1.76 (m, 9H), 1.42-1.48 (m, 2H) ppm.

Example 2

2-(5-Chloro-pyridin-2-ylamino)-thiazole-4-carboxylic acid [(E)-5-hydroxyadamantan-2-yl]-amide

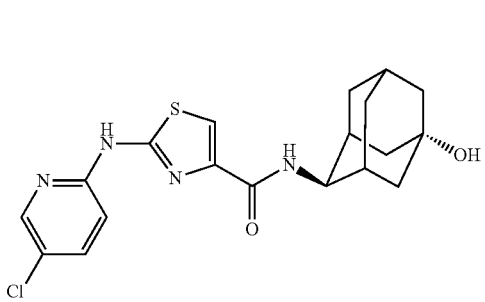 [SMILES: O=C(N[C@H]1C2CC3CC1C[C@](O)(C3)C2)c1csc(Nc2ccc(Cl)cn2)n1]

5-Chloro-pyridin-2-ylamine (1.0 g) and Fmoc-NCS (2.4 g) in dichloromethane:tetra-hydrofuran (1:1, 15 mL) was stirred at reflux for about 8 hours. The precipitate was filtered and washed with dichloromethane:hexanes (1:1, 500 mL). A dichloromethane (30 mL) solution of the precipitate was stirred with piperidine (2.5 mL) at room temperature for about 2 hours. The reaction product was concentrated and washed with dichloromethane:hexanes (1:1, 200 mL) to give (5-chloro-pyridin-2-yl)-thiourea (1.0 g).

2-(5-Chloro-pyridin-2-ylamino)-thiazole-4-carboxylic acid ethyl ester (1.0 g) was prepared according to General Procedure C using (5-chloro-pyridin-2-yl)-thiourea (1.0 g) and 3-bromo-2-oxo-propionic acid ethyl ester (1.07 g) in methanol (15 mL). The crude product was washed with a dichloromethane:hexane (1:1, 200 mL) solution to give a substantially pure product. 2-(5-Chloro-pyridin-2-ylamino)-thiazole-4-carboxylic acid (76 mg) was prepared according to General Procedure C using 2-(5-chloro-pyridin-2-ylamino)-thiazole-4-carboxylic acid ethyl ester (100 mg) in methanol:tetrahydrofuran (1:1, 2 mL) and 2N sodium hydroxide in water (0.5 mL). The crude product was used in subsequent steps without further purification.

2-(5-Chloro-pyridin-2-ylamino)-thiazole-4-carboxylic acid [(E)-5-hydroxy-adamantan-2-yl]-amide (30 mg) was prepared according to General Procedure D using 2-(5-chloro-pyridin-2-ylamino)-thiazole-4-carboxylic acid (76 mg), DIEA (0.1 mL), HBTU (145 mg) and a 3:1 mixture of E- and Z-4-amino-adamantan-1-ol (65 mg) in dimethylformamide (2 mL). The crude product was purified by automated flash chromatography on a prepacked silica (12 g) column using hexanes:ethyl acetate as the eluent to give the title compound.

LC-MS (m/z): 405 (M+1)$^+$; $^1$H NMR (400 MHz, DMSO-d$_6$): δ 8.35 (d, 1H), 7.81 (m, H), 7.62 (s, 1H), 7.51-7.57 (m, 1H), 7.05-7.11 (m, 1H), 4.48 (s, 1H), 3.89-3.95 (m, 1H), 2.04 (br. s., 3H), 1.60-1.77 (m, 9H), 1.40-1.49 (m, 2H) ppm.

Example 3

2-(Pyridin-4-ylamino)-thiazole-4-carboxylic acid [(E)-5-hydroxy-adamantan-2-yl]-amide

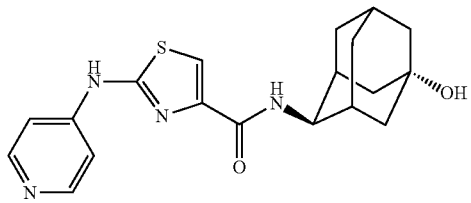 [SMILES: O=C(N[C@H]1C2CC3CC1C[C@](O)(C3)C2)c1csc(Nc2ccncc2)n1]

2-(Pyridin-4-ylamino)-thiazole-4-carboxylic acid ethyl ester (200 mg) was prepared according to General Procedure B using pyridin-4-yl-thiourea (154 mg) and 3-bromo-2-oxo-propionic acid ethyl ester (200 mg) in methanol (2 mL). The crude product was used without further purification.

2-(Pyridin-4-ylamino)-thiazole-4-carboxylic acid (160 mg) was prepared according to General Procedure C using 2-(pyridin-4-ylamino)-thiazole-4-carboxylic acid ethyl ester in methanol:tetrahydrofuran:2N NaOH (1:1:1, 1.5 mL). The solvents were evaporated and the compound was dried. The crude product was used without further purification.

2-(Pyridin-4-ylamino)-thiazole-4-carboxylic acid [(E)-5-hydroxy-adamantan-2-yl]-amide (115 mg) was prepared according to General Procedure D using 2-(pyridin-4-ylamino)-thiazole-4-carboxylic acid (110 mg), DIEA (0.26 mL), HBTU (208 mg) and (E)-4-amino-adamantan-1-ol hydrochloride (111 mg) in dimethylformamide (1 mL). The crude product was purified by automated flash chromatography on a prepacked silica (12 g) column using hexanes:ethyl acetate as the eluent to give the title compound.

LC-MS (m/z): 371 (M+1)$^+$; $^1$H NMR (400 MHz, methanol-d$_4$): δ 8.43 (d, 2H), 7.86 (d, 2H), 7.78 (s, 1H), 4.08 (br. s., 1H), 2.15-2.26 (m, 3H), 1.76-1.93 (m, 9H), 1.62 (m, 2H) ppm. (amide NH and hydroxy OH not observed).

Example 4

2-(Pyridin-3-ylamino)-thiazole-4-carboxylic acid [(E)-5-hydroxy-adamantan-2-yl]-amide

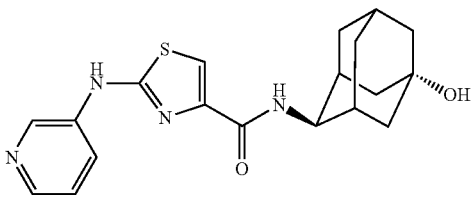 [SMILES: O=C(N[C@H]1C2CC3CC1C[C@](O)(C3)C2)c1csc(Nc2cccnc2)n1]

2-(Pyridin-3-ylamino)-thiazole-4-carboxylic acid ethyl ester (200 mg) was prepared according to General Procedure B using pyridin-3-yl-thiourea (154 mg) and 3-bromo-2-oxo-propionic acid ethyl ester (200 mg) in methanol (2 mL). The crude product was used in subsequent steps without further purification.

2-(Pyridin-3-ylamino)-thiazole-4-carboxylic acid (165 mg) was prepared according to General Procedure C using 2-(pyridin-3-ylamino)-thiazole-4-carboxylic acid ethyl ester in methanol:tetrahydrofuran:2N NaOH (1:1:1, 1.5 mL). The solvents were evaporated and the compound was dried. The crude product was used without further purification.

2-(Pyridin-3-ylamino)-thiazole-4-carboxylic acid [(E)-5-hydroxy-adamantan-2-yl]-amide (100 mg) was prepared according to General Procedure D using 2-(pyridin-3-ylamino)-thiazole-4-carboxylic acid (110 mg), DIEA (0.26 mL), HBTU (208 mg) and (E)-4-amino-adamantan-1-ol hydrochloride (111 mg) in dimethylformamide (1 mL). The crude product was purified by automated flash chromatography on a prepacked silica (12 g) column using hexanes:ethyl acetate as the eluent to give the title compound.

LC-MS (m/z): 370.94 (M+1)+; $^1$H NMR (400 MHz, methanol-$d_4$): δ 8.87 (d, 1H), 8.19 (d, 1H), 8.10-8.14 (m, 1H), 7.81-7.86 (m, 1H), 7.56 (s, 1H), 7.44 (m, 1H), 4.07-4.12 (m, 1H), 2.20 (br. s., 2H), 1.77-1.94 (m, 9H), 1.64 (m, 2H) ppm (amide NH and hydroxy OH not observed).

Example 5

2-(Pyridin-2-ylamino)-thiazole-4-carboxylic acid [(E)-5-hydroxy-adamantan-2-yl]-amide

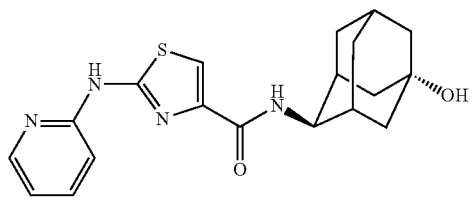 [SMILES: O=C(N[C@H]1C2CC3CC1C[C@](O)(C3)C2)c1csc(Nc2ccccn2)n1]

2-(Pyridin-2-ylamino)-thiazole-4-carboxylic acid ethyl ester (195 mg) was prepared according to General Procedure C using pyridin-2-yl-thiourea (154 mg) and 3-bromo-2-oxo-propionic acid ethyl ester (200 mg) in methanol (2 mL). 2-(Pyridin-2-ylamino)-thiazole-4-carboxylic acid (160 mg) was prepared according to General Procedure C using 2-(pyridin-2-ylamino)-thiazole-4-carboxylic acid ethyl ester in methanol:tetrahydrofuran:2N NaOH (1:1:1, 1.5 mL). The solvents were evaporated and the compound was dried. The crude product was used in a subsequent step without further purification.

2-(Pyridin-2-ylamino)-thiazole-4-carboxylic acid [(E)-5-hydroxy-adamantan-2-yl]-amide (100 mg) was prepared according to General Procedure D using 2-(pyridin-2-ylamino)-thiazole-4-carboxylic acid (110 mg), DIEA (0.26 mL), HBTU (208 mg) and (E)-4-amino-adamantan-1-ol hydrochloride (111 mg) in dimethylformamide (2 mL). The crude product was purified by automated flash chromatography on a prepacked silica (12 g) column using hexanes:ethyl acetate as the eluent to give the title compound.

LC-MS (m/z): 370.94 (M+1)+; $^1$H NMR (400 MHz, methanol-$d_4$): δ 8.28-8.35 (m, 1H), 7.65-7.72 (m, 1H), 7.58 (s, 1H), 6.89-6.99 (m, 2H), 4.08-4.12 (m, 1H), 2.11-2.21 (m, 3H), 1.80 (br. s., 9H), 1.56-1.64 (m, 2H) ppm (amide NH and hydroxy OH not observed).

Example 6

2-(2-Phenyl-ethylamino)-thiazole-4-carboxylic acid [(E)-5-hydroxy-adamantan-2-yl]-amide

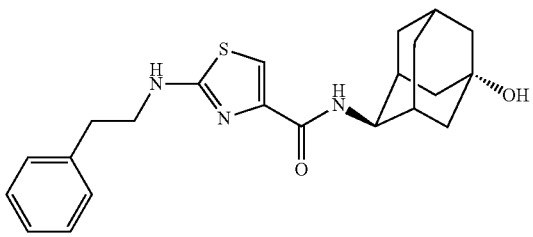

2-Phenethylamino-thiazole-4-carboxylic acid (235 mg) was prepared according to General Procedure B using phenethyl-thiourea (180 mg) and 3-bromo-2-oxo-propionic acid (167 mg) in methanol (2 mL). The crude product was used in a subsequent step without further purification.

2-(2-Phenyl-ethylamino)-thiazole-4-carboxylic acid [(E)-5-hydroxy-adamantan-2-yl]-amide (95 mg) was prepared according to General Procedure D using 2-phenethylamino-thiazole-4-carboxylic acid (100 mg), DIEA (0.20 mL), HBTU (167 mg) and (E)-4-amino-adamantan-1-ol hydrochloride (89 mg) in dimethylformamide (2 mL). The crude product was purified by automated flash chromatography on a prepacked silica (12 g) column using hexanes:ethyl acetate as the eluent to give the title compound.

LC-MS (m/z): 398 (M+1)+; $^1$H NMR (400 MHz, DMSO-$d_6$): δ 7.97-8.02 (m, 1H), 7.54-7.59 (m, 1H), 7.21-7.34 (m, 5H), 4.49-4.54 (m, 1H), 3.88-3.94 (m, 1H), 3.42-3.50 (m, 2H), 2.89 (m, 2H), 1.99-2.08 (m, 3H), 1.66 (m, 9H), 1.43-1.51 (m, 2H) ppm.

Example 7

2-(2-Pyridin-2-yl-ethylamino)-thiazole-4-carboxylic acid [(E)-5-hydroxy-adamantan-2-yl]-amide

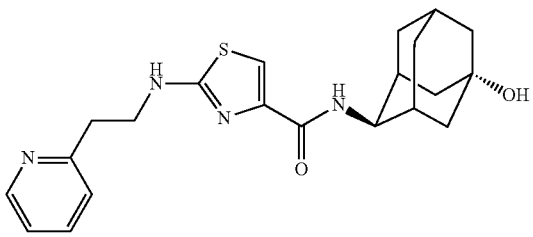 [SMILES: O=C(N[C@H]1C2CC3CC1C[C@](O)(C3)C2)c1csc(NCCc2ccccc2)n1]

2-(2-Pyridin-2-yl-ethylamino)-thiazole-4-carboxylic acid (375 mg) was prepared according to General Procedure B using (2-pyridin-2-yl-ethyl)-thiourea (300 mg) and 3-bromo-2-oxo-propionic acid (295 mg) in methanol (3 mL). The crude product was used in a subsequent step without further purification.

2-(2-Pyridin-2-yl-ethylamino)-thiazole-4-carboxylic acid [(E)-5-hydroxy-adamantan-2-yl]-amide (95 mg) was prepared according to General Procedure D using 2-(2-pyridin-2-yl-ethylamino)-thiazole-4-carboxylic acid (100 mg), DIEA (0.20 mL), HBTU (182 mg) and (E)-4-amino-adamantan-1-ol hydrochloride (93 mg) in dimethylformamide (2 mL). The crude product was purified by automated flash chromatography on a prepacked silica (12 g) column using a mixture of dichloromethane, ethyl acetate, and methanol as the eluent to give the title compound.

LC-MS (m/z): 398.81 (M+1)+; 1H NMR (400 MHz, CDCl3): δ 8.56-8.60 (m, 1H), 7.64 (m, 1H), 7.47-7.54 (m, 1H), 7.29 (s, 1H), 7.20 (d, 2H), 6.04-6.10 (m, 1H), 4.10-4.17 (m, 1H), 3.70-3.75 (m, 2H), 3.12-3.18 (m, 2H), 2.20 (br s., 3H), 1.91 (br. m., 2H), 1.76-1.84 (m, 6H), 1.50-1.57 (m, 3H) ppm.

Example 8

2-(4-Trifluoromethyl-phenylamino)-thiazole-4-carboxylic acid [(E)-5-hydroxy-adamantan-2-yl]-amide

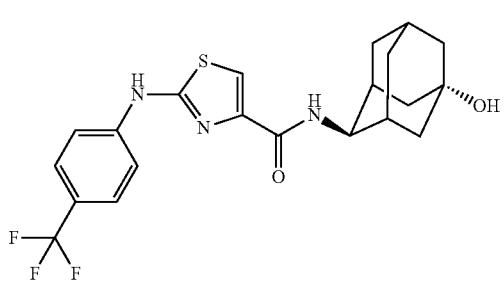 [SMILES: O=C(N[C@H]1C2CC3CC1C[C@](O)(C3)C2)c1csc(Nc2ccc(C(F)(F)F)cc2)n1]

2-(4-Trifluoromethyl-phenylamino)-thiazole-4-carboxylic acid (275 mg) was prepared according to General Procedure B using (4-trifluoromethyl-phenyl)-thiourea (220 mg) and 3-bromo-2-oxo-propionic acid (200 mg) in methanol (2 mL). The crude product was used in a subsequent step without further purification.

2-(4-Trifluoromethyl-phenylamino)-thiazole-4-carboxylic acid [(E)-5-hydroxy-adamantan-2-yl]-amide (75 mg) was prepared according to General Procedure D using 2-(4-trifluoromethyl-phenylamino)-thiazole-4-carboxylic acid (100 mg), DIEA (0.20 ml), HBTU (151 mg) and (E)-4-amino-adamantan-1-ol hydrochloride (77 mg) in dimethylformamide (1 mL). The crude product was purified by automated flash chromatography on a prepacked silica (12 g) column using hexanes:ethyl acetate as the eluent to give the title compound.

LC-MS (m/z): 438 (M+1)+; 1H NMR (400 MHz, methanol-d4): δ 7.87-7.91 (m, 1H), 7.77 (d, 2H), 7.60 (d, 2H), 7.56 (s, 1H), 4.07-4.12 (m, 1H), 2.17-2.24 (br. s, 3H), 1.80-1.92 (m, 9H), 1.61-1.67 (m, 2H) ppm (amide NH not observed).

Example 9

2-(4-Methoxy-phenylamino)-thiazole-4-carboxylic acid [(E)-5-hydroxy-adamantan-2-yl]-amide

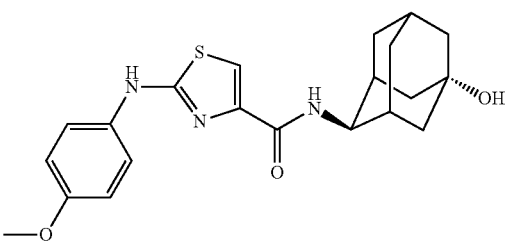 [SMILES: COc1ccc(Nc2nc(C(=O)N[C@H]3C4CC5CC3C[C@](O)(C5)C4)cs2)cc1]

2-(4-Methoxy-phenylamino)-thiazole-4-carboxylic acid (237 mg) was prepared according to General Procedure B using (4-methoxy-phenyl)-thiourea (182 mg) and 3-bromo-2-oxo-propionic acid (200 mg) in methanol (2 mL). The crude product was used in a subsequent step without further purification.

2-(4-Methoxy-phenylamino)-thiazole-4-carboxylic acid [(E)-5-hydroxy-adamantan-2-yl]-amide (60 mg) was prepared according to General Procedure D using 2-(4-methoxy-phenylamino)-thiazole-4-carboxylic acid (75 mg), DIEA (0.15 mL), HBTU (117 mg) and (E)-4-amino-adamantan-1-ol hydrochloride (63 mg) in dimethylformamide (1 mL). The crude product was purified by automated flash chromatography on a prepacked silica (12 g) column using hexanes:ethyl acetate as the eluent to give the title compound.

LC-MS (m/z): 400 (M+1)+; 1H NMR (400 MHz, methanol-d4): δ 7.89-7.95 (m, 1H), 7.41-7.47 (d, 2H), 7.36 (s, 1H), 6.87-6.93 (d, 2H), 4.03-4.10 (m, 1H), 3.78 (s, 3H), 2.16 (br s., 3H), 1.77-1.95 (m, 9H), 1.62 (br m., 2H) ppm (amide NH not observed).

Example 10

2-(4-Chloro-phenylamino)-thiazole-4-carboxylic acid [(E)-5-hydroxy-adamantan-2-yl]-amide

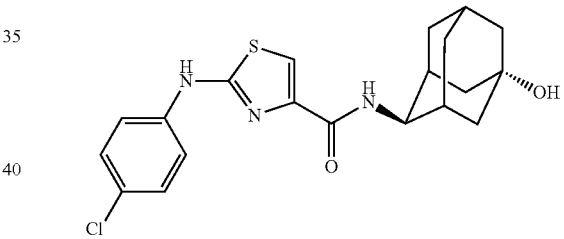

2-(4-Chloro-phenylamino)-thiazole-4-carboxylic acid (240 mg) was prepared according to General Procedure B using (4-chloro-phenyl)-thiourea (186 mg) and 3-bromo-2-oxo-propionic acid (200 mg) in methanol (2 mL). The crude product was used in a subsequent step without further purification.

2-(4-Chloro-phenylamino)-thiazole-4-carboxylic acid [(E)-5-hydroxy-adamantan-2-yl]-amide (94 mg) was prepared according to General Procedure D using 2-(4-chloro-phenylamino)-thiazole-4-carboxylic acid (100 mg), DIEA (0.2 mL), HBTU (162 mg) and (E)-4-amino-adamantan-1-ol hydrochloride (88 mg) in dimethylformamide (1 mL). The crude product was purified by automated flash chromatography on a prepacked silica (12 g) column using hexanes:ethyl acetate as the eluent to give the title compound.

LC-MS (m/z): 404 (M+1)+; 1H NMR (400 MHz, methanol-d4): δ 7.58 (d, 2H), 7.49 (s, 1H), 7.30 (d, 2H), 4.06-4.11 (m, 1H), 2.17-2.22 (m, 3H), 1.80 (m, 9H), 1.60-1.67 (m, 2H) ppm (amide NH and hydroxy OH not observed).

Example 11

2-(4-Fluoro-phenylamino)-thiazole-4-carboxylic acid [(E)-5-hydroxy-adamantan-2-yl]-amide

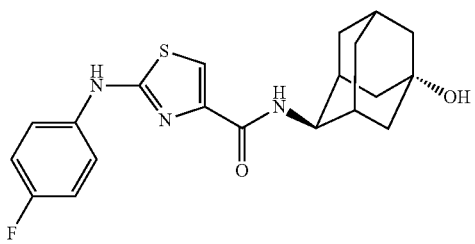 [SMILES: O=C(N[C@H]1C2CC3CC1C[C@](O)(C3)C2)c1csc(Nc2ccc(F)cc2)n1]

2-(4-Fluoro-phenylamino)-thiazole-4-carboxylic acid (224 mg) was prepared according to General Procedure B using (4-fluoro-phenyl)-thiourea (170 mg) and 3-bromo-2-oxo-propionic acid (200 mg) in methanol (2 mL). The crude product was used in a subsequent step without further purification.

2-(4-Fluoro-phenylamino)-thiazole-4-carboxylic acid [(E)-5-hydroxy-adamantan-2-yl]-amide (90 mg) was prepared according to General Procedure D using 2-(4-fluoro-phenylamino)-thiazole-4-carboxylic acid (100 mg), DIEA (0.21 mL), HBTU (174 mg) and (E)-4-amino-adamantan-1-ol hydrochloride (93 mg) in dimethylformamide (1 mL). The crude product was purified by automated flash chromatography on a prepacked silica (12 g) column using hexanes:ethyl acetate as the eluent to give the title compound.

LC-MS (m/z): 388 (M+1)$^+$; $^1$H NMR (400 MHz, methanol-$d_4$): δ 7.89 (d, 1H), 7.53-7.60 (m, 2H), 7.43 (s, 1H), 7.03-7.10 (m, 2H), 4.07 (m, 1H), 2.17 (br s., 3H), 1.86-1.94 (m, 2H), 1.81 (m, 6H), 1.62 (d, 2H) ppm (amide NH and hydroxy OH not observed).

Example 12

2-(3,4-Dichloro-phenylamino)-thiazole-4-carboxylic acid [(E)-5-hydroxy-adamantan-2-yl]-amide

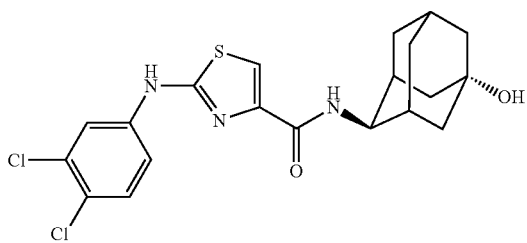 [SMILES: O=C(N[C@H]1C2CC3CC1C[C@](O)(C3)C2)c1csc(Nc2ccc(Cl)c(Cl)c2)n1]

2-(3,4-Dichloro-phenylamino)-thiazole-4-carboxylic acid (275 mg) was prepared according to General Procedure B using (3,4-dichloro-phenyl)-thiourea (220 mg) and 3-bromo-2-oxo-propionic acid (200 mg) in methanol (2 mL). The crude product was used in a subsequent step without further purification.

2-(3,4-Dichloro-phenylamino)-thiazole-4-carboxylic acid [(E)-5-hydroxy-adamantan-2-yl]-amide (40 mg) was prepared according to General Procedure D using 2-(3,4-dichloro-phenylamino)-thiazole-4-carboxylic acid (50 mg), DIEA (0.1 mL), HBTU (72 mg) and (E)-4-amino-adamantan-1-ol hydrochloride (40 mg) in dimethylformamide (1 mL). The crude product was purified by automated flash chromatography on a prepacked silica (12 g) column using hexanes:ethyl acetate as the eluent to give the title compound.

LC-MS (m/z): 438 (M+1)$^+$; $^1$H NMR (400 MHz, methanol-$d_4$): δ 8.31 (d, 1H), 7.86-7.91 (m, 1H), 7.52 (s, 1H), 7.41 (d, 1H), 7.19 (m, 1H), 4.08-4.14 (m, 1H), 2.18 (br s., 3H) 1.91 (m, 4H), 1.78-1.85 (m, 4H), 1.59-1.68 (m, 2H) ppm (amide NH and hydroxy OH not observed).

Example 13

2-[(Pyridin-3-ylmethyl)-amino]-thiazole-4-carboxylic acid [(E)-5-hydroxy-adamantan-2-yl]-amide

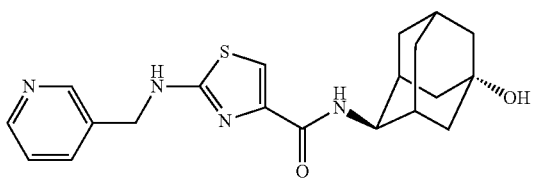 [SMILES: O=C(N[C@H]1C2CC3CC1C[C@](O)(C3)C2)c1csc(NCc2cccnc2)n1]

Pyridin-3-ylmethyl-thiourea (217 mg) was prepared according to General Procedure A using C-pyridin-3-yl-methylamine (215 mg) and Fmoc-NCS (618 mg) in dichloromethane (5 mL).

2-[(Pyridin-3-ylmethyl)-amino]hiazole-4-carboxylic acid (134 mg) was prepared according to General Procedure B using pyridin-3-ylmethyl-thiourea (100 mg) and 3-bromo-2-oxo-propionic acid (110 mg) in methanol (2 mL). The crude product was used in a subsequent step without further purification.

2-[(Pyridin-3-ylmethyl)-amino]-thiazole-4-carboxylic acid [(E)-5-hydroxy-adamantan-2-yl]-amide (80 mg) was prepared according to General Procedure D using 2-[(pyridin-3-ylmethyl)-amino]-thiazole-4-carboxylic acid (100 mg), DIEA (0.2 mL), HBTU (182 mg) and (E)-4-amino-adamantan-1-ol hydrochloride (95 mg) in dimethylformamide (2 mL). The crude product was purified by automated flash chromatography on a prepacked silica (12 g) column using hexanes:ethyl acetate as the eluent to yield the title compound.

LC-MS (m/z): 385 (M+1)$^+$; $^1$H NMR (400 MHz, CDCl$_3$): δ 8.65 (d, 1H), 8.57 (dd, 1H), 7.73 (d, 1H), 7.42-7.48 (m, 1H), 7.31-7.34 (s, 1H), 5.57 (m, 1H), 4.56 (d, 2H), 4.11 (br m., 1H), 2.18 (br. s., 3H), 1.89-1.96 (m, 2H), 1.75-1.83 (m, 6H), 1.49-1.57 (m, 3H) ppm (amide NH not observed).

Example 14

2-Benzylamino-thiazole-4-carboxylic acid [(E)-5-hydroxy-adamantan-2-yl]-amide

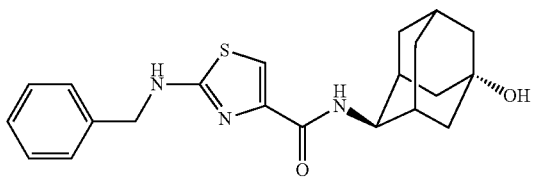 [SMILES: O=C(N[C@H]1C2CC3CC1C[C@](O)(C3)C2)c1csc(NCc2ccccc2)n1]

2-Benzylamino-thiazole-4-carboxylic acid [(E)-5-hydroxy-adamantan-2-yl]-amide (110 mg) was prepared according to General Procedure D using 2-benzylamino-thiazole-4-carboxylic acid (100 mg), DIEA (0.2 mL), HBTU (182 mg) and (E)-4-amino-adamantan-1-ol hydrochloride (95 mg) in dimethylformamide (2 mL). The crude product was purified by automated flash chromatography on a prepacked silica (12 g) column using hexanes:ethyl acetate as the eluent to give the title compound.

LC-MS (m/z): 383.83 (M+1)$^+$; $^1$H NMR (400 MHz, CDCl$_3$): δ 7.46-7.51 (m, 1H), 7.36-7.40 (m, 3H), 7.32-7.36 (m, 1H), 7.31 (s, 1H), 5.38-5.44 (m, 1H), 4.49 (d, 2H), 4.11-4.16 (m, 1H), 2.19 (br s., 3H), 1.89-1.96 (m, 2H), 1.76-1.82 (m, 6H), 1.51 (m, 3H) ppm (amide NH not observed).

Example 15

2-(2-Pyridin-3-yl-ethylamino)-thiazole-4-carboxylic acid [(E)-5-hydroxy-adamantan-2-yl]-amide

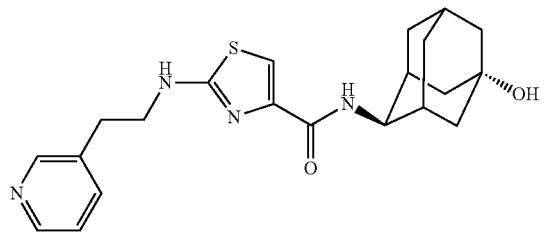

(2-Pyridin-3-yl-ethyl)-thiourea (300 mg) was prepared according to General Procedure A using 2-pyridin-3-yl-ethylamine (250 mg) and Fmoc-NCS (576 mg) in dichloromethane (5 mL).

2-(2-Pyridin-3-yl-ethylamino)-thiazole-4-carboxylic acid (236 mg) was prepared according to General Procedure B using 2-pyridin-3-yl-ethyl)-thiourea (300 mg) and 3-bromo-2-oxo-propionic acid (295 mg) in methanol (2 mL). The crude product was used in a subsequent step without further purification.

2-(2-Pyridin-3-yl-ethylamino)-thiazole-4-carboxylic acid [(E)-5-hydroxy-adamantan-2-yl]-amide (87 mg) was prepared according to General Procedure D using 2-(2-pyridin-3-yl-ethylamino)-thiazole-4-carboxylic acid (100 mg), DIEA (0.2 mL), HBTU (185 mg) and (E)-4-amino-adamantan-1-ol hydrochloride (95 mg) in dimethylformamide (2 mL). The crude product was purified by automated flash chromatography on a prepacked silica (12 g) column using a mixture of dichloromethane, ethyl acetate, and methanol as the eluent to give the title compound.

LC-MS (m/z): 398.81 (M+1)$^+$; $^1$H NMR (400 MHz, methanol-d$_4$): δ 8.33-8.44 (m, 2H), 7.70-7.78 (m, 1H), 7.32-7.39 (m, 1H), 7.23 (s, 1H), 3.98-4.04 (m, 1H), 3.59 (br t, 2H), 2.97 (br., t, 2H), 2.11 (br. s., 3H), 1.72-1.90 (m, 9H), 1.49-1.58 (m, 2H) ppm. (amide NH and hydroxy OH not observed).

Example 16

2-(2-Pyridin-4-yl-ethylamino)-thiazole-4-carboxylic acid [(E)-5-hydroxy-adamantan-2-yl]-amide

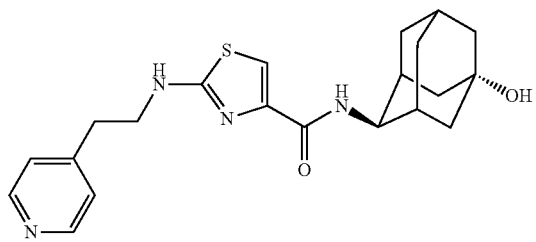 [SMILES: O=C(N[C@H]1C2CC3CC1C[C@](O)(C3)C2)c1csc(NCCc2ccncc2)n1]

(2-Pyridin-4-yl-ethyl)-thiourea (300 mg) was prepared according to General Procedure A using 2-pyridin-4-yl-ethylamine (250 mg) and Fmoc-NCS (576 mg) in dichloromethane (5 mL).

2-(2-Pyridin-4-yl-ethylamino)-thiazole-4-carboxylic acid (236 mg) was prepared according to General Procedure B using (2-pyridin-4-yl-ethyl)-thiourea (300 mg) and 3-bromo-2-oxo-propionic acid (293 mg) in methanol (2 mL). The crude product was used in a subsequent step without further purification.

2-(2-Pyridin-4-yl-ethylamino)-thiazole-4-carboxylic acid [(E)-5-hydroxy-adamantan-2-yl]-amide (80 mg) was prepared according to General Procedure D using 2-(2-pyridin-4-yl-ethylamino)-thiazole-4-carboxylic acid (100 mg), DIEA (0.2 mL), HBTU (182 mg) and (E)-4-amino-adamantan-1-ol hydrochloride (93 mg) in dimethylformamide (2 mL). The crude product was purified by automated flash chromatography on a prepacked silica (12 g) column using a mixture of dichloromethane, ethyl acetate, and methanol as the eluent to give the title compound.

LC-MS (m/z): 398.81 (M+1)$^+$; $^1$H NMR (400 MHz, CDCl$_3$): δ 8.56 (d, 2H) 7.47 (d, 1H), 7.34 (s, 1H), 7.18 (d, 2H), 5.15 (br t, 1H), 4.14 (br d, 1H), 3.63 (q, 2H), 3.00 (t, 2H), 2.16-2.24 (br m, 3H), 1.90-1.97 (br d, 2H), 1.77-1.84 (br m, 6H), 1.54 (br d, 3H) ppm.

Example 17

2-(5-Chloro-pyridin-2-ylamino)-thiazole-5-carboxylic acid [(E)-5-hydroxy-adamantan-2-yl]-amide

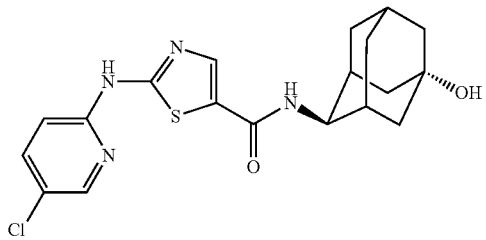 [SMILES: O=C(N[C@H]1C2CC3CC1C[C@](O)(C3)C2)c1cnc(Nc2ccc(Cl)cn2)s1]

2-(5-Chloro-pyridin-2-ylamino)-thiazole-5-carboxylic acid ethyl ester (1.0 g) was prepared according to General Procedure C using (5-chloro-pyridin-2-yl)-thiourea (938 mg) and 2-chloro-3-oxo-propionic acid ethyl ester (900 mg) in benzene (15 mL). The crude product was washed with dichloromethane:hexane (1:1, 200 mL) solution to give a substantially pure product. 2-(5-Chloro-pyridin-2-ylamino)-thiazole-5-carboxylic acid (663 mg) was prepared according to General Procedure C using 2-(5-Chloro-pyridin-2-ylamino)-thiazole-5-carboxylic acid ethyl ester (1.0 g) in methanol:tetrahydrofuran:2N NaOH (1:1:1, 6 mL). The crude product was used in a subsequent step without further purification.

2-(5-Chloro-pyridin-2-ylamino)-thiazole-5-carboxylic acid [(E)-5-hydroxy-adamantan-2-yl]-amide (5 mg) was prepared according to General Procedure D using 2-(5-Chloro-pyridin-2-ylamino)-thiazole-5-carboxylic acid (300 mg), DIEA (0.6 mL), HBTU (500 mg) and (E)-4-amino-adamantan-1-ol hydrochloride (260 mg) in dimethylformamide (3 mL). The crude product was purified by automated flash chromatography on a prepacked silica (12 g) column using hexanes:ethyl acetate as the eluent to give the title compound.

LC-MS (m/z): 405 (M+1)$^+$; $^1$H NMR (400 MHz, methanol-d$_4$): δ 8.32-8.37 (m, 1H), 8.04-8.07 (m, 1H), 7.71-7.76 (m, 1H), 7.02-7.08 (m, 1H), 4.04-4.08 (m, 1H), 2.20-2.26 (m, 2H), 2.11-2.16 (m, 1H), 1.97-2.04 (m, 2H), 1.85-1.91 (m, 2H), 1.77 (br. s., 5H) 1.49-1.56 (m, 2H), 1.34-1.38 (m, 1H), 1.27-1.31 (m, 1H) ppm.

Example 18

4-Methyl-2-phenethylamino-thiazole-5-carboxylic acid [(E)-5-hydroxy-adamantan-2-yl]-amide

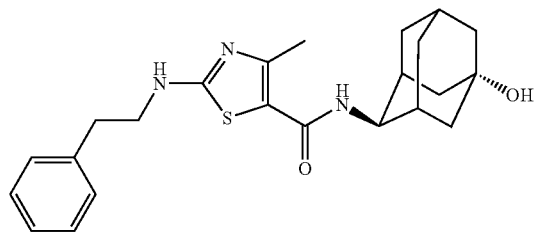 [SMILES: Cc1nc(NCCc2ccccc2)sc1C(=O)N[C@H]1C2CC3CC1C[C@](O)(C3)C2]

4-Methyl-2-phenethylamino-thiazole-5-carboxylic acid [(E)-5-hydroxy-adamantan-2-yl]-amide (110 mg) was prepared according to General Procedure D using 4-methyl-2-phenethylamino-thiazole-5-carboxylic acid (130 mg), DIEA (0.26 mL), HBTU (230 mg) and (E)-4-amino-adamantan-1-ol hydrochloride (105 mg) in dimethylformamide (2 mL). The crude product was purified using hexane:ethyl acetate solvent system on a pre-packed (12 g) silica column.

LC-MS (m/z): 412 (M+1)$^+$; $^1$H NMR (400 MHz, methanol-d$_4$): δ 7.15-7.32 (m, 5H), 7.04 (d, 1H), 3.98 (br s., 1H), 3.51 (t, 2H), 2.91 (t, 2H), 2.43 (s, 3H), 2.08-2.21 (m, 3H), 1.73-1.94 (m, 8H), 1.52 (d, 2H), 1.36 (d, 2H) ppm.

The compounds recited above having a basic group or acidic group are depicted as the free base or acid. Depending on the reaction conditions and purification conditions, various compounds having a basic group may have been isolated in either the free base form, as a salt (such as a hydrochloride salt), or in both forms.

As shown in Table 1, below, compounds of the invention inhibit 11βHSD1 enzyme activity. Compounds that inhibit 11βHSD1 enzyme activity are potentially useful in treating diseases, disorders, or conditions where modulation of 11βHSD1 is beneficial, such as metabolic syndrome, type 2 diabetes, impaired glucose tolerance (IGT), impaired fasting glucose (IFG), dyslipidemia, obesity, hypertension, diabetic late complications, cardiovascular diseases, arteriosclerosis, atherosclerosis, myopathy, muscle wasting, osteoporosis, neurodegenerative and psychiatric disorders, adverse effects of treatment or therapy with glucocorticoid receptor agonists, and dysregulation of intraocular pressure including glaucoma.

The compounds of Formula (I) and/or pharmaceutically acceptable salts thereof may therefore be useful in the treatment of one or more of these diseases.

Pharmaceutical Compositions

In one embodiment, the present invention provides a pharmaceutical composition comprising a compound of Formula (I) or a pharmaceutically acceptable salt thereof. In another embodiment, the present invention provides a pharmaceutical composition comprising a compound of any one of embodiments 1 to 22 (recited above). In another embodiment, the pharmaceutical composition comprises a compound of any one of embodiments 1 to 22 and a pharmaceutically acceptable carrier, excipient, diluent, or a mixture thereof. In some embodiments, the invention provides a pharmaceutical composition in unit dosage form comprising from 0.01 mg to 1000 mg of a compound of any one of embodiments 1 to 22 and a pharmaceutically acceptable carrier. In some other embodiments, the invention provides a liquid pharmaceutical composition comprising from 100 μg/mL to 10 mg/mL of a compound of any one of embodiments 1 to 22 and a pharmaceutically acceptable carrier. In some such embodiments, the pharmaceutically acceptable carrier is an aqueous medium. In some such embodiments, the pharmaceutically acceptable carrier is water.

In an embodiment, the pharmaceutical compositions containing a compound of Formula (I) or a pharmaceutically acceptable salt thereof may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, to form osmotic therapeutic tablets for controlled release.

In another embodiment, formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

In another embodiment, the composition may comprise an aqueous suspension. Aqueous suspensions may contain the active compounds in an admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Also, oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

In another embodiment, the pharmaceutical compositions of the present invention may comprise a syrup or elixir. Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

In an embodiment, the pharmaceutical compositions of the present invention may comprise an aqueous solution, where the solution comprises the active ingredient in a solubilized form. In some such embodiments, the pharmaceutical composition may also contain an amount of non-solubilized active ingredient (e.g., suspended in the aqueous solution). In other such embodiments, the pharmaceutical composition contains the active ingredient such that substantially all of the active ingredient is solubilized in the aqueous solution (e.g., at least 95%, or at least 97%, or at least 99%, or at least 99.5%, or at least 99.8% (by moles) based on the total amount of active ingredient present in the pharmaceutical composition. Such solutions may be useful for topical use, such as to the skin or the eye.

Pharmaceutically-acceptable salts of compounds of Formula (I), where a basic or acidic group is present in the structure, are also included within the scope of the invention. The term "pharmaceutically acceptable salts" refers to salts of the compounds of this invention which are not biologically or otherwise undesirable and are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, there can be formed an acidic salt, such as hydrochloride, hydrobromide, phosphate, sulfate, trifluoroacetate, trichloroacetate, acetate, oxalate, maleate, pyruvate, malonate, succinate, citrate, tartarate, fumarate, mandelate, benzoate, cinnamate, methanesulfonate, ethanesulfonate, picrate and the like, and include acids related to the pharmaceutically-acceptable salts listed in Berge, S. M., et al., "Pharmaceutical Salts" 66(1) *J. Pharm. Sci.* 1-19 (1977).

In another embodiment, the invention provides a pharmaceutical composition comprising a compound of Formula (I) or a pharmaceutically acceptable salt thereof and one or more pharmaceutically acceptable carriers, excipients, or diluents. In another embodiment, the invention provides a pharmaceutical composition comprising a compound of any one of embodiments 1 to 22 and one or more pharmaceutically acceptable carriers, excipients, or diluents.

In another embodiment, the present invention provides a compound of Formula (I) or a pharmaceutically acceptable salt thereof for use in medicine. In another embodiment, the invention provides a compound of any one of embodiments 1 to 22 for use in medicine.

The present invention further provides for the use of a compound of Formula (I) or a pharmaceutically acceptable salt thereof in combination with one or more medically effective active compounds for simultaneous, subsequent, or sequential administration. The invention also provides for the use of a compound of any one of embodiments 1 to 22 in combination with one or more medically effective active compounds for simultaneous, subsequent, or sequential administration.

Examples of such medically effective active ingredients include, but are not limited to, antiobesity agents, antidiabetics, agents modifying the lipid metabolism, antihypertensive agents, glucocorticoid receptor agonists, agents for the treatment and/or prevention of complications resulting from or associated with diabetes and agents for the treatment and/or prevention of complications and disorders resulting from or associated with obesity.

Suitable antiobesity agents or apetite regulating agents include, but are not limited to, CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, H3 histamine antagonists, opioid antagonists (such as naltrexone), exendin-4, GLP-1 and ciliary neurotrophic factor. Further examples of suitable antiobesity agents include leptin; dexamphetamine or amphetamine; fenfluramine or dexfenfluramine; sibutramine; orlistat; mazindol or phentermine.

Suitable antidiabetic agents include, but are not limited to, insulin, insulin analogues and derivatives such as those disclosed in EP 792 290 (Novo Nordisk A/S), e.g. $N^{\epsilon B29}$-tetradecanoyl des (B30) human insulin, EP 214 826 and EP 705 275 (Novo Nordisk A/S), e.g. $Asp^{B28}$ human insulin, U.S. Pat. No. 5,504,188 (Eli Lilly), e.g. $Lys^{B28}$ $Pro^{B29}$ human insulin, EP 368 187 (Aventis), eg Lantus, which are all incorporated herein by reference, GLP-1 (glucagon like peptide-1) and GLP-1 derivatives such as those disclosed in WO 98/08871 to Novo Nordisk A/S, which is incorporated herein by reference as well as orally active hypoglycemic agents. The orally active hypoglycemic agents may comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as PPARα modulators, PPARδ modulators, cholesterol absorption inhibitors, HSL (hormone-sensitive lipase) inhibitors and HMG CoA inhibitors (statins), nicotinic acid, fibrates, anion exchangers, compounds lowering food intake, bile acid resins, RXR agonists and agents acting on the ATP-dependent potassium channel of the β-cells.

In some embodiments, a compound of any one of embodiments 1 to 22 is administered in combination with insulin or an insulin analogue or derivative, such as $N^{\epsilon B29}$-tetradecanoyl des (B30) human insulin, $Asp^{B28}$ human insulin, $Lys^{B28}$ $Pro^{B29}$ human insulin, LANTUS, or a mix-preparation comprising one or more of these.

In a further embodiment a compound of any one of embodiments 1 to 22 is administered in combination with a sulphonylurea e.g. tolbutamide, glibenclamide, glipizide or glicazide.

In another embodiment a compound of any one of embodiments 1 to 22 is administered in combination with a biguanide e.g. metformin.

In yet another embodiment a compound of any one of embodiments 1 to 22 is administered in combination with a meglitinide e.g. repaglinide or senaglinide.

In still another embodiment a compound of any one of embodiments 1 to 22 is administered in combination with a thiazolidinedione e.g. troglitazone, ciglitazone, pioglitazone, rosiglitazone or compounds disclosed in WO 97/41097 such as 5-[[4-[3-Methyl-4-oxo-3,4-dihydro-2-quinazolinyl]methoxy]phenyl-methyl]thiazolidine-2,4-dione or a pharmaceutically acceptable salt thereof, such as the potassium salt.

In yet another embodiment a compound of any one of embodiments 1 to 22 is administered in combination with the insulin sensitizers disclosed in WO 99/19313 such as (−)3-[4-[2-phenoxazin-10-yl)ethoxy]phenyl]-2-ethoxypropanoic acid or a pharmaceutically acceptable salts thereof, such as the arginine salt.

In a further embodiment a compound of any one of embodiments 1 to 22 is administered in combination with an α-glucosidase inhibitor e.g. miglitol or acarbose.

In another embodiment a compound of any one of embodiments 1 to 22 is administered in combination with an agent acting on the ATP-dependent potassium channel of the β-cells e.g. tolbutamide, glibenclamide, glipizide, glicazide or repaglinide.

Furthermore, a compound of any one of embodiments 1 to 22 is administered in combination with nateglinide.

In still another embodiment a compound of any one of embodiments 1 to 22 is administered in combination with an antihyperlipidemic agent or antilipidemic agent e.g. cholestyramine, colestipol, clofibrate, gemfibrozil, fenofibrate, bezafibrate, tesaglitazar, EML-4156, LY-818, MK-767, atorvastatin, fluvastatin, lovastatin, pravastatin, simvastatin, acipimox, probucol, ezetimibe or dextrothyroxine.

In a further embodiment a compound of any one of embodiments 1 to 22 is administered in combination with more than one of the above-mentioned compounds e.g. in combination with a sulphonylurea and metformin, a sulphonylurea and acarbose, repaglinide and metformin, insulin and a sulphonylurea, insulin and metformin, insulin, insulin and lovastatin, etc.

Further, a compound of any one of embodiments 1 to 22 is administered in combination with one or more antihypertensive agents. Examples of antihypertensive agents are β-blockers such as alprenolol, atenolol, timolol, pindolol, propranolol, metoprolol, bisoprololfumerate, esmolol, acebutelol, metoprolol, acebutolol, betaxolol, celiprolol, nebivolol, tertatolol, oxprenolol, amusolalul, carvedilol, labetalol, β2-receptor blockers e.g. S-atenolol, OPC-1085, ACE (angiotensin converting enzyme) inhibitors such as quinapril, lisinopril, enalapril, captopril, benazepril, perindopril, trandolapril, fosinopril, ramipril, cilazapril, delapril, imidapril, moexipril, spirapril, temocapril, zofenopril, S-5590, fasidotril, Hoechst-Marion Roussel: 100240 (EP 00481522), omapatrilat, gemopatrilat and GW-660511, calcium channel blockers such as nifedipine, felodipine, nicardipine, isradipine, nimodipine, diltiazem, amlodipine, nitrendipine, verapamil, lacidipine, lercanidipine, aranidipine, cilnidipine, clevidipine, azelnidipine, barnidipine, efonodipine, iasidipine, iemildipine, iercanidipine, manidipine, nilvadipine, pranidipine, furnidipine, α-blockers such as doxazosin, urapidil, prazosin, terazosin, bunazosin and OPC-28326, diuretics such as thiazides/sulphonamides (e.g. bendro-flumetazide, chlorothalidone, hydrochlorothiazide and clopamide), loop-diuretics (e.g. bumetanide, furosemide and torasemide) and potassium sparing diuretics (e.g. amiloride, spironolactone), endothelin ET-A antagonists such as ABT-546, ambrisetan, atrasentan, SB-234551, CI-1034, S-0139 and YM-598, endothelin antagonists e.g. bosentan and J-104133, renin inhibitors such as aliskiren, vasopressin V1 antagonists e.g. OPC-21268, vasopressin V2 antagonists such as tolvaptan, SR-121463 and OPC-31260, B-type natriuretic peptide agonists e.g. Nesiritide, angiotensin II antagonists such as irbesartan, candesartancilexetil, losartan, valsartan, telmisartan, eprosartan, candesartan, CL-329167, eprosartan, iosartan, olmesartan, pratosartan, TA-606, and YM-358, 5-HT2 agonists e.g. fenoldopam and ketanserin, adenosine A1 antagonists such as naftopidil, N-0861 and FK-352, thromboxane A2 antagonists such as KT2-962, endopeptidase inhibitors e.g. ecadotril, nitric oxide agonists such as LP-805, dopamine D1 antagonists e.g. MYD-37, dopamine D2 agonists such as nolomirole, n-3 fatty acids e.g. omacor, prostacyclin agonists such as treprostinil, beraprost, PGE1 agonists e.g. ecraprost, Na$^+$/K$^+$ ATPase modulators e.g. PST-2238, Potassium channel activators e.g. KR-30450, vaccines such as PMD-3117, Indapamides, CGRP-unigene, guanylate cyclase stimulators, hydralazines, methyldopa, docarpamine, moxonidine, CoAprovel, MondoBiotech-811.

Furthermore, a compound of any one of embodiments 1 to 22 is administered in combination with one or more glucocorticoid receptor agonists. Examples of such glucocorticoid receptor agonists are betametasone, dexamethasone, hydrocortisone, methylprednisolone, prednisolone, prednisone, beclomethasone, butixicort, clobetasol, flunisolide, flucatisone (and analogues), mometasone, triamcinolonacetonide, triamcinolonhexacetonide GW-685698, NXC-1015, NXC-1020, NXC-1021, NS-126, P-4112, P-4114, RU-24858 and T-25 series.

Methods of Use

A compound of Formula (I) or pharmaceutically acceptable salt thereof, a pharmaceutical composition comprising a compound of Formula (I), a pharmaceutically acceptable salt of a compound of formula (I), or a pharmaceutical composition comprising a pharmaceutically acceptable salt of a compound of Formula (I), may be used for the treatment of a disease, disorder, or condition selected from the group consisting of metabolic syndrome, type 2 diabetes, impaired glucose tolerance (IGT), impaired fasting glucose (IFG), dyslipidemia, obesity, hypertension, diabetic late complications, cardiovascular diseases, arteriosclerosis, atherosclerosis, myopathy, muscle wasting, osteoporosis, neurodegenerative and psychiatric disorders, adverse effects of treatment or therapy with glucocorticoid receptor agonists, and dysregulation of intraocular pressure including glaucoma.

In one embodiment, the invention provides a method of treatment comprising administering a compound of any one of embodiments 1 to 22 to a human. In another embodiment, the invention provides a method of treatment comprising administering at least 0.1 milligrams of a compound of any one of embodiments 1 to 22 to a human. In another embodiment, the invention provides a method of treatment of any of the diseases, disorders, or conditions described below, comprising administering an effective amount of a compound of any one of embodiments 1 to 22 to a subject (e.g., a human). As used herein, the term "effective amount" is an amount sufficient to induce the desired therapeutic effect in a subject to whom the compound is administered.

In another embodiment, the invention provides a method of treatment comprising administering a compound of any one of embodiments 1 to 22 to a human, so as to treat at least one disorder selected from the group consisting of metabolic syndrome, type 2 diabetes, impaired glucose tolerance (IGT), impaired fasting glucose (IFG), dyslipidemia, obesity, hypertension, diabetic late complications, cardiovascular diseases, arteriosclerosis, atherosclerosis, myopathy, muscle wasting, osteoporosis, neurodegenerative and psychiatric disorders, adverse effects of treatment or therapy with glucocorticoid receptor agonists, and dysregulation of intraocular pressure including glaucoma. In another embodiment, the invention provides a method of treatment comprising administering a compound of any one of embodiments 1 to 22 to a human, so as to treat metabolic syndrome. In another embodiment, the invention provides a method of treatment comprising administering a compound of any one of embodiments 1 to 22 to a human, so as to treat type 2 diabetes. In another embodiment, the invention provides a method of treatment comprising administering a compound of any one of embodiments 1 to 22 to a human, so as to treat adverse effects of treatment or therapy with glucocorticoid receptor agonists. In another embodiment, the invention provides a method of treatment comprising administering a compound of any one of embodiments 1 to 22 to a human, so as to treat dysregulation of intraocular pressure including glaucoma. In another embodiment, the invention provides a method of treatment comprising administering a compound of any one of embodiments 1 to 22 to a human, so as to reduce intraocular pressure.

In another embodiment, the invention provides a compound of any one of embodiments 1 to 22 for use in medicine. In another embodiment, the invention provides a compound of any one of embodiments 1 to 22 for use in the treatment of at least one disease, disorder, or condition selected from the group consisting of metabolic syndrome, type 2 diabetes, impaired glucose tolerance (IGT), impaired fasting glucose (IFG), dyslipidemia, obesity, hypertension, diabetic late complications, cardiovascular diseases, arteriosclerosis, atherosclerosis, myopathy, muscle wasting, osteoporosis, neurodegenerative and psychiatric disorders, adverse effects of treatment or therapy with glucocorticoid receptor agonists, and dysregulation of intraocular pressure including glaucoma. In another embodiment, the invention provides a compound of any one of embodiments 1 to 22 for use in the treatment of metabolic syndrome. In another embodiment, the invention provides a compound of any one of embodiments 1 to 22 for use in the treatment of type 2 diabetes. In another embodiment, the invention provides a compound of any one of embodiments 1 to 22 for use in the treatment of adverse effects of treatment or therapy with glucocorticoid receptor agonists. In another embodiment, the invention provides a compound of any one of embodiments 1 to 22 for use in the treatment of dysregulation of intraocular pressure including glaucoma. In another embodiment, the invention provides a compound of any one of embodiments 1 to 22 for use in the reducing intraocular pressure.

In another embodiment, the invention provides a compound of any one of embodiments 1 to 22 for use in the prevention of at least one disease, disorder, or condition selected from the group consisting of metabolic syndrome, type 2 diabetes, impaired glucose tolerance (IGT), impaired fasting glucose (IFG), dyslipidemia, obesity, hypertension, diabetic late complications, cardiovascular diseases, arteriosclerosis, atherosclerosis, myopathy, muscle wasting, osteoporosis, neurodegenerative and psychiatric disorders, adverse effects of treatment or therapy with glucocorticoid receptor agonists, and dysregulation of intraocular pressure including glaucoma. In another embodiment, the invention provides a compound of any one of embodiments 1 to 22 for use in the prevention of metabolic syndrome. In another embodiment, the invention provides a compound of any one of embodiments 1 to 22 for use in the prevention of type 2 diabetes. In another embodiment, the invention provides a compound of any one of embodiments 1 to 22 for use in the prevention of adverse effects of treatment or therapy with glucocorticoid receptor agonists. In another embodiment, the invention provides a compound of any one of embodiments 1 to 22 for use in the prevention of dysregulation of intraocular pressure including glaucoma.

In another embodiment, the invention provides for the use of a compound of any one of embodiments 1 to 22 for the preparation of a medicament. In another embodiment, the invention provides for the use of a compound of any one of embodiments 1 to 22 for the preparation of a medicament for the treatment of at least one disease, disorder, or condition selected from the group consisting of metabolic syndrome, type 2 diabetes, impaired glucose tolerance (IGT), impaired fasting glucose (IFG), dyslipidemia, obesity, hypertension, diabetic late complications, cardiovascular diseases, arteriosclerosis, atherosclerosis, myopathy, muscle wasting, osteoporosis, neurodegenerative and psychiatric disorders, adverse effects of treatment or therapy with glucocorticoid receptor agonists, and dysregulation of intraocular pressure including glaucoma. In another embodiment, the invention provides for the use of a compound of any one of embodiments 1 to 22 for the preparation of a medicament for the treatment of metabolic disorder. In another embodiment, the invention provides for the use of a compound of any one of embodiments 1 to 22 for the preparation of a medicament for the treatment of type 2 diabetes. In another embodiment, the invention provides for the use of a compound of any one of embodiments 1 to 22 for the preparation of a medicament for the treatment of adverse effects of treatment or therapy with glucocorticoid receptor agonists. In another embodiment, the invention provides for the use of a compound of any one of embodiments 1 to 22 for the preparation of a medicament for the treatment of dysregulation of intraocular pressure including glaucoma. In another embodiment, the invention provides for the use of a compound of any one of embodiments 1 to 22 for the preparation of a medicament for reducing intraocular pressure.

In another embodiment, the present invention provides a method for reducing intracellular glucocorticoid levels in a human tissue. In one embodiment, the invention provides a method of reducing intracellular glucocorticoid levels in a human tissue comprising administering a compound of any one of embodiments 1 to 22 to a human.

In another embodiment, the present invention provides a method for reducing intraocular pressure. In one embodiment, the invention provides a method of reducing intraocular pressure comprising administering a compound of any one of embodiments 1 to 22 to a human.

In each of the methods or uses described above, a compound of any of embodiments 1 to 22 may be administered to a subject as part of a pharmaceutically formulation, as described above.

Examples of compounds of Formula (I) or pharmaceutically acceptable salts thereof having potentially useful biological activity are listed by name below in Table 1. The ability of compounds Formula (I) or pharmaceutically acceptable salts thereof to inhibit 11βHSD1 was established with the representative compounds of Formula (I) listed in Table 1 using the assays described below.

Biological Assays

The following assay methods were used to identify and evaluate compounds of Formula (I) that are effective in modulating 11βHSD1.

Materials:
96 well ½ area well plate (Fisher #07-200-329)
CISBIO Cortisol kit #62CO2PEB Buffers:
Assay Buffer: (water based) used for Enzyme, Compounds and Microsomes: 20 mM Tris, 5 mM EDTA, and pH 6.0.
Enzyme Buffer: 333 μM NADPH (FAC 200 μM) and 266 nM Cortisone (FAC 160 nM).

Protocol:
1) Test compounds (10 mM stock in 100% DMSO) were diluted in Assay Buffer (see below) with 1% DMSO FAC and placed into the 96-well plate. Test compounds were typically tested over 10 concentrations (30 μM-0.3 nM).
2) 30 μL Enzyme Buffer, 10 μL Test Compound, 10 μL human microsomes were added to the test compounds and mixed gently by tapping the plate.
3) The plates were incubated for 2 h at 37° C.
4) 25 μL anti Cortisol-K and 25 μL Cortisol d2 were added to the plate and mixed gently by tapping the plate.
5) The plates were incubated at room temperature for 2 h.
6) The plates were read on an Envision model 2120 Perkin-Elmer using emission filters #205 and #217. Data is calculated as a change in delta F, shown in Table 1.

TABLE 1

| Example | in vitro 11β-HSD Assay [$EC_{50}$ (nM)] |
|---------|------------------------------------------|
| 1  | 360  |
| 2  | 31   |
| 3  | 110  |
| 4  | 26   |
| 5  | 4000 |
| 6  | 11   |
| 7  | 127  |
| 8  | 13   |
| 9  | 2    |
| 10 | 8.7  |
| 11 | 2.7  |
| 12 | 112  |
| 13 | 39   |
| 14 | 78   |
| 15 | 165  |
| 16 | 369  |
| 17 | 31   |
| 18 | 48   |

Human Adipocytes Cell Based Assay

Cells were ordered from ZenBio, RTP, NC (www.zenbio.com (OA-1096-3)) pre-plated (96 well). Cell Media was supplied by ZenBio (Omental Adipocyte Medium #OM-AM).

Test compounds were prepared at 10 concentrations (10 μM-0.1 nM). Dilutions were made up in Cell Media. Cell Media from the plate is aspirated and 97 μL was added to the wells.

The plates were incubated for 15 minutes (37° C.).

3 μL of 10 mM cortisone (Sigma #C2755) (300 nM FAC) was added, for a total well volume of 100 μL.

The plates were incubated for 24 hours (37° C.).

The media was harvested from cells.

The samples were then assayed using Cortisol ELISA Kits (R & D Systems #SKGE008). Samples were diluted by a factor of 5. Specific instructions were included in the kit to quantify presence of cortisol in samples through an ELISA assay.

The plates were read on a Spectramax at 450 nm OD.

Example 2 had an average $IC_{50}$ value of 19 nM.

While the invention has been described and illustrated with reference to certain embodiments thereof, those skilled in the art will appreciate that various changes, modifications and substitutions can be made therein without departing from the spirit and scope of the invention. For example, effective dosages other than the dosages as set forth herein may be applicable as a consequence of variations in the responsiveness of the subject being treated. Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention. Moreover, all compounds that are recited in the written description are contemplated as possibilities for any of the recited methods, processes, compositions, and/or compounds as appear in the written description and the appended claims.

We claim:

1. A compound of formula (I) or a pharmaceutically acceptable salt thereof:

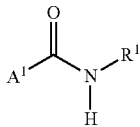

(I)

wherein $R^1$ is 5-hydroxy-adamantan-2-yl;

$R^2$ is aryl, heteroaryl, —$C_{1-4}$ alkylene-aryl, or —$C_{1-4}$ alkylene-heteroaryl, where the aryl and heteroaryl groups are optionally substituted one or more times with substituents selected independently from the group consisting of halogen, $C_{1-4}$ alkyl, —O—$C_{1-4}$ alkyl, —$CF_3$, —$CH_2CF_3$, —$CF_2CF_3$, and —$OCF_3$;

$A^1$ is

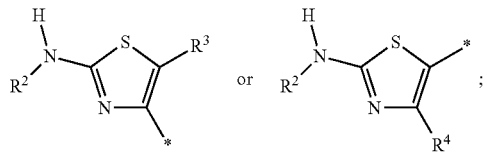

and $R^3$ and $R^4$ are each independently selected from the group consisting of hydrogen, halogen, $C_{1-4}$ alkyl, —O—$C_{1-4}$ alkyl, —$CF_3$, —$CH_2CF_3$, —$CF_2CF_3$, and —$OCF_3$.

2. The compound of claim 1, wherein $A^1$ is

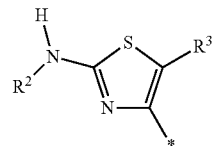

and $R^3$ is hydrogen.

3. The compound of claim 2, wherein $R^2$ is phenyl optionally substituted one or two times with substituents selected independently from the group consisting of halogen, $C_{1-4}$ alkyl, —O—$C_{1-4}$ alkyl, —$CF_3$, —$CH_2CF_3$, —$CF_2CF_3$, and —$OCF_3$.

4. The compound of claim 2, wherein $R^2$ is 2-pyridyl, 3-pyridyl, or 4-pyridyl, each of which is optionally substituted one or more times with substituents selected independently from the group consisting of halogen, $C_{1-4}$ alkyl, —O—$C_{1-4}$ alkyl, —$CF_3$, —$CH_2CF_3$, —$CF_2CF_3$, and —$OCF_3$.

5. The compound of claim 4, wherein $R^2$ is 2-pyridyl, 3-pyridyl, or 4-pyridyl, each of which is substituted one or two times with chloro.

6. The compound of claim 2, wherein $R^2$ is phenethyl or benzyl.

7. The compound of claim 2, wherein $R^2$ is —$CH_2$-(3-pyridyl), —$CH_2CH_2$-(2-pyridyl), —$CH_2CH_2$-(3-pyridyl), or —$CH_2CH_2$-(4-pyridyl).

8. A compound selected from the group consisting of:
2-[(furan-2-ylmethyl)-amino]-thiazole-4-carboxylic acid [(E)-5-hydroxy-adamantan-2-yl]-amide;
2-(5-chloro-pyridin-2-ylamino)-thiazole-4-carboxylic acid [(E)-5-hydroxyadamantan-2-yl]-amide;
2-(pyridin-4-ylamino)-thiazole-4-carboxylic acid [(E)-5-hydroxy-adamantan-2-yl]-amide;
2-(pyridin-3-ylamino)-thiazole-4-carboxylic acid [(E)-5-hydroxy-adamantan-2-yl]-amide;
2-(pyridin-2-ylamino)-thiazole-4-carboxylic acid [(E)-5-hydroxy-adamantan-2-yl]-amide;
2-(2-phenyl-ethylamino)-thiazole-4-carboxylic acid [(E)-5-hydroxy-adamantan-2-yl]-amide;
2-(2-pyridin-2-yl-ethylamino)-thiazole-4-carboxylic acid [(E)-5-hydroxy-adamantan-2-yl]-amide;
2-(4-trifluoromethyl-phenylamino)-thiazole-4-carboxylic acid [(E)-5-hydroxy-adamantan-2-yl]-amide;
2-(4-methoxy-phenylamino)-thiazole-4-carboxylic acid [(E)-5-hydroxy-adamantan-2-yl]-amide;
2-(4-chloro-phenylamino)-thiazole-4-carboxylic acid [(E)-5-hydroxy-adamantan-2-yl]-amide;
2-(4-fluoro-phenylamino)-thiazole-4-carboxylic acid [(E)-5-hydroxy-adamantan-2-yl]-amide;
2-(3,4-dichloro-phenylamino)-thiazole-4-carboxylic acid [(E)-5-hydroxy-adamantan-2-yl]-amide;
2-[(pyridin-3-ylmethyl)-amino]-thiazole-4-carboxylic acid [(E)-5-hydroxy-adamantan-2-yl]-amide;
2-benzylamino-thiazole-4-carboxylic acid [(E)-5-hydroxy-adamantan-2-yl]-amide;
2-(2-pyridin-3-yl-ethylamino)-thiazole-4-carboxylic acid [(E)-5-hydroxy-adamantan-2-yl]-amide;
2-(2-pyridin-4-yl-ethylamino)-thiazole-4-carboxylic acid [(E)-5-hydroxy-adamantan-2-yl]-amide;
2-(5-chloro-pyridin-2-ylamino)-thiazole-5-carboxylic acid [(E)-5-hydroxy-adamantan-2-yl]-amide; and
4-methyl-2-phenethylamino-thiazole-5-carboxylic acid [(E)-5-hydroxy-adamantan-2-yl]-amide;
or a pharmaceutically acceptable salt thereof.

9. 2-(5-Chloro-pyridin-2-ylamino)-thiazole-4-carboxylic acid [(E)-5-hydroxy-adamantan-2-yl]-amide or a pharmaceutically acceptable salt thereof.

10. The compound of claim 9, wherein the compound is 2-(5-chloro-pyridin-2-ylamino)-thiazole-4-carboxylic acid [(E)-5-hydroxyadamantan-2-yl]-amide.

11. The compound of claim 9, wherein the compound is a pharmaceutically acceptable salt of 2-(5-chloro-pyridin-2-ylamino)-thiazole-4-carboxylic acid [(E)-5-hydroxyadamantan-2-yl]-amide.

12. 2-(Pyridin-3-ylamino)-thiazole-4-carboxylic acid [(E)-5-hydroxy-adamantan-2-yl]-amide or a pharmaceutically acceptable salt thereof.

13. The compound of claim 12, wherein the compound is 2-(pyridin-3-ylamino)-thiazole-4-carboxylic acid [(E)-5-hydroxy-adamantan-2-yl]-amide.

14. The compound of claim 12, wherein the compound is a pharmaceutically acceptable salt of 2-(pyridin-3-ylamino)-thiazole-4-carboxylic acid [(E)-5-hydroxy-adamantan-2-yl]-amide.

15. 2-(2-Phenyl-ethylamino)-thiazole-4-carboxylic acid [(E)-5-hydroxy-adamantan-2-yl]-amide or a pharmaceutically acceptable salt thereof.

16. The compound of claim 15, wherein the compound is 2-(2-phenyl-ethylamino)-thiazole-4-carboxylic acid [(E)-5-hydroxy-adamantan-2-yl]-amide.

17. The compound of claim 15, wherein the compound is a pharmaceutically acceptable salt of 2-(2-phenyl-ethylamino)-thiazole-4-carboxylic acid [(E)-5-hydroxy-adamantan-2-yl]-amide.

18. 2-(4-Trifluoromethyl-phenylamino)-thiazole-4-carboxylic acid [(E)-5-hydroxy-adamantan-2-yl]-amide or a pharmaceutically acceptable salt thereof.

19. The compound of claim 18, wherein the compound is 2-(4-trifluoromethyl-phenylamino)-thiazole-4-carboxylic acid [(E)-5-hydroxy-adamantan-2-yl]-amide.

20. The compound of claim 18, wherein the compound is a pharmaceutically acceptable salt of 2-(4-trifluoromethyl-phenylamino)-thiazole-4-carboxylic acid [(E)-5-hydroxy-adamantan-2-yl]-amide.

21. 2-(4-Methoxy-phenylamino)-thiazole-4-carboxylic acid [(E)-5-hydroxy-adamantan-2-yl]-amide or a pharmaceutically acceptable salt thereof.

22. The compound of claim 21, wherein the compound is 2-(4-methoxy-phenylamino)-thiazole-4-carboxylic acid [(E)-5-hydroxy-adamantan-2-yl]-amide.

23. The compound of claim 21, wherein the compound is a pharmaceutically acceptable salt of 2-(4-methoxy-phenylamino)-thiazole-4-carboxylic acid [(E)-5-hydroxy-adamantan-2-yl]-amide.

24. 2-(4-Fluoro-phenylamino)-thiazole-4-carboxylic acid [(E)-5-hydroxy-adamantan-2-yl]-amide or a pharmaceutically acceptable salt thereof.

25. The compound of claim 24, wherein the compound is 2-(4-fluoro-phenylamino)-thiazole-4-carboxylic acid [(E)-5-hydroxy-adamantan-2-yl]-amide.

26. The compound of claim 24, wherein the compound is a pharmaceutically acceptable salt of 2-(4-fluoro-phenylamino)-thiazole-4-carboxylic acid [(E)-5-hydroxy-adamantan-2-yl]-amide.

27. A pharmaceutical composition comprising a compound of claim 1 and a pharmaceutically acceptable carrier.

28. A pharmaceutical composition comprising a compound of claim 8 and a pharmaceutically acceptable carrier.

29. A pharmaceutical composition comprising a compound of claim 9 and a pharmaceutically acceptable carrier.

30. A pharmaceutical composition comprising a compound of claim 12 and a pharmaceutically acceptable carrier.

31. A pharmaceutical composition comprising a compound of claim 15 and a pharmaceutically acceptable carrier.

32. A pharmaceutical composition comprising a compound of claim 18 and a pharmaceutically acceptable carrier.

33. A pharmaceutical composition comprising a compound of claim 21 and a pharmaceutically acceptable carrier.

34. A pharmaceutical composition comprising a compound of claim 24 and a pharmaceutically acceptable carrier.

35. A method of treating a disease, disorder, or condition comprising administering to a subject an amount of a compound of claim 1, where the disease, disorder, or condition is selected from the group consisting of: metabolic syndrome, type 2 diabetes, impaired glucose tolerance (IGT), impaired fasting glucose (IFG), dyslipidemia, obesity, hypertension, arteriosclerosis, atherosclerosis, myopathy, muscle wasting, osteoporosis, adverse effects of treatment or therapy with glucocorticoid receptor agonists, and dysregulation of intraocular pressure including glaucoma.

36. A method of treating metabolic syndrome comprising administering to a subject an amount of a compound of claim 1.

37. A method of treating type 2 diabetes comprising administering to a subject an amount of a compound of claim 1.

38. A method of treating the adverse effects of treatment or therapy with a glucocorticoid receptor agonist comprising administering to a subject an amount of a compound of claim 1.

39. A method of treating a dysregulation of intraocular pressure, including glaucoma, comprising administering to a subject an amount of a compound of claim 1.

40. A method of reducing intracellular glucocorticoid levels in a human tissue comprising administering to a subject an amount of a compound of claim 1.

41. A method of reducing intraocular pressure comprising administering to a subject an amount of a compound of claim 1.

* * * * *